US008680256B2

(12) United States Patent
Abu Khabar

(10) Patent No.: US 8,680,256 B2
(45) Date of Patent: Mar. 25, 2014

(54) METHODS FOR PRODUCING INDUCIBLE AND/OR REPRESSIBLE EXPRESSION ACTIVE LINEAR RNA INTERFERENCE CASSETTES AND INDUCIBLE AND/OR REPRESSIBLE EXPRESSION ACTIVE LINEAR GENE CASSETTES AND THEIR USES

(75) Inventor: Khalid S. Abu Khabar, Riyadh (SA)

(73) Assignee: King Faisal Specialist Hospital & Research Centre, Riyadh (SA)

( * ) Notice: Subject to any disclaimer, the term of this patent is extended or adjusted under 35 U.S.C. 154(b) by 0 days.

(21) Appl. No.: 13/001,303

(22) PCT Filed: May 25, 2009

(86) PCT No.: PCT/EP2009/003686
§ 371 (c)(1),
(2), (4) Date: Mar. 15, 2011

(87) PCT Pub. No.: WO2009/156030
PCT Pub. Date: Dec. 30, 2009

(65) Prior Publication Data
US 2011/0166042 A1    Jul. 7, 2011

(30) Foreign Application Priority Data

Jun. 27, 2008  (WO) ................ PCT/EP2008/005278
Nov. 17, 2008  (WO) ................ PCT/EP2008/009712

(51) Int. Cl.
*C12N 15/64* (2006.01)
*C07H 21/04* (2006.01)

(52) U.S. Cl.
USPC ....................................... 536/24.1; 435/91.4

(58) Field of Classification Search
None
See application file for complete search history.

(56) References Cited

U.S. PATENT DOCUMENTS 6,177,611 B1    1/2001  Rice
2008/0097088 A1*  4/2008  Simpson et al. ............. 536/24.1

FOREIGN PATENT DOCUMENTS

| WO | WO 01/21834    | 3/2001  |
| WO | WO 2004/013288 | 2/2004  |
| WO | WO 2005/000888 | 1/2005  |
| WO | WO 2005/095615 | 10/2005 |
| WO | WO 2006/081831 | 8/2006  |
| WO | WO 2006/123097 | 11/2006 |

OTHER PUBLICATIONS

Sykes et al., Linear expression elements: a rapid, in vivo, method to screen for gene functions; Nature Biotech, vol. 17, pp. 355-359, 1999.*
Kappel et al., Silencing of mammalian genes by tetracyclineinducible shRNA expression; Nature Protocols, vol. 2 No. 12, pp. 3257-3269, 2007.*
Meyer-Ficca et al., Comparative analysis of inducible expression systems in transient transfection studies; Anal. Biochem., vol. 334, pp. 9-19, 2004.*
Wang et al., Nitric oxide-p38 MAPK signaling stabilizes mRNA through AU-rich element-dependent and -independent mechanisms; J Leukocyte Biology, vol. 83, No. 4, pp. 982-990, 2008.*
Arif et al., "A functional genomic analysis of calcium homeostasis in *Escherichia coli*", Abstracts of the General Meeting of the American Society of Microbiology, 101st General Meeting of the American Society for Microbiology, Orlando, Fl., May 20-24, 2001, abstract.
Castanotto et al., "Functional siRNA expression from transfected PCR products," *RNA*, Jan. 2002, vol. 8, No. 11, pp. 1454-1460.
Han et al., "Endotoxin-responsive sequences control cachectin/tumor necrosis factor biosynthesis at the translational level", *Journal of Experimental Medicine*, Feb. 1990, vol. 171, No. 2, pp. 465-475.
He et al., "Interference of porcine reproductive and respiratory syndrome virus replication on MARC-145 cells using DNA-based short interfering RNAs," *Antiviral Research*, May 2007, vol. 74, No. 2, pp. 83-91.
Lu et al., "Gene expression enhancement mediated by the 5' UTR intron of the rice *rubi3* gene varied remarkably among tissues in transgenic rice plants", *Molecular Genetics and Genomics*, Jun. 2008, vol. 279, No. 6, pp. 563-572.
Moor et al., "Mechanisms of translational control by the 3' UTR in development and differentiation", *Seminars in Cell & Developmental Biology*, Feb. 2005, vol. 16, No. 1, pp. 49-58.
Roa-Rodríguez, "Promoters used to regulate gene expression," retrieved from the Internet: URL: http://www.patentlens.net/daisy/promoters/768.html>, Apr. 11, 2007, 191 pages.
Sambrook et al., "Molecular Cloning", *Cold Spring Harbor Laboratory Press*, 2001, 3rd edition, pp. 8.37-8.45, 9.36-9.37, 17.30-17.51, XP-002497435.
Wilkie et al.,"Regulation of mRNA translation by 5'- and 3'-UTR-binding factors", *TRENDS in Biochemical Sciences*, Apr. 2003, vol. 28, No. 4, pp. 182-188.
Yoshihama et al., "The human ribosomal protein genes: sequencing and comparative analysis of 73 genes", *Genome Research*, Mar. 2002, vol. 12, No. 3, pp. 379-390.

* cited by examiner

*Primary Examiner* — Celine Qian
*Assistant Examiner* — Addison D Ault
(74) *Attorney, Agent, or Firm* — Saliwanchik, Lloyd & Eisenschenk

(57) ABSTRACT

The present invention relates to a (first) method for producing inducible and/or repressible expression active linear RNA interference constructs comprising a PCR amplification of a source polynucleotide comprising the inhibitory RNA coding sequence of interest or comprising a PCR amplification of a DNA source comprising a promoter using a reverse primer comprising the inhibitory RNA coding sequence of interest. The present invention furthermore relates to a (second) method for producing inducible and/or repressible expression active linear gene constructs comprising a PCR amplification of a source expression polynucleotide comprising a promoter sequence and the DNA sequence of interest or comprising a PCR amplification using the DNA sequence as a template. The present invention furthermore relates to libraries, arrays, cells and cell lines and kits utilizing the inducible and/or repressible expression active linear RNA interference constructs or the inducible and/or repressible expression active linear gene constructs.

21 Claims, 8 Drawing Sheets

METHODS FOR PRODUCING INDUCIBLE AND/OR REPRESSIBLE EXPRESSION ACTIVE LINEAR RNA INTERFERENCE CASSETTES AND INDUCIBLE AND/OR REPRESSIBLE EXPRESSION ACTIVE LINEAR GENE CASSETTES AND THEIR USES

CROSS REFERENCE TO A RELATED APPLICATION

This application is a National Stage Application of International Application Number PCT/EP2009/003686, filed May 25, 2009; which claims priority to International Patent Application PCT/EP2008/005278, filed Jun. 27, 2008 and International Application No. PCT/EP2008/009712, filed Nov. 17, 2008; all of which are incorporated herein by reference in their entirety.

The Sequence Listing for this application is labeled "SeqList.txt" which was created on Dec. 22, 2010 and is 23 KB. The entire content of the sequence listing is incorporated herein by reference in its entirety.

The present invention relates to a (first) method for producing inducible and/or repressible expression active linear RNA interference constructs comprising a PCR amplification of a source polynucleotide comprising the inhibitory RNA coding sequence of interest or comprising a PCR amplification of a DNA source comprising a promoter using a reverse primer comprising the inhibitory RNA coding sequence of interest. The present invention furthermore relates to a (second) method for producing inducible and/or repressible expression active linear gene constructs comprising a PCR amplification of a source expression polynucleotide comprising a promoter sequence and the DNA sequence of interest or comprising a PCR amplification using the DNA sequence as a template. The present invention furthermore relates to libraries, arrays, cells and cell lines and kits utilizing the inducible and/or repressible expression active linear RNA interference constructs or the inducible and/or repressible expression active linear gene constructs.

BACKGROUND OF THE INVENTION

RNA interference (RNAi) is a system within living cells that helps to control which genes are active and how active they are. Two types of small RNA molecules—micro RNA (miRNA) and small interfering RNA (siRNA)—are central to RNA interference. RNAs are the direct products of genes, and these small RNAs can bind to specific other RNAs and either increase or decrease their activity, for example by preventing a messenger RNA (mRNA) from producing a protein. RNA interference has an important role in defending cells against parasitic genes but also in directing development as well as gene expression in general.

The RNAi pathway is found in many eukaryotes and is initiated by the enzyme Dicer which cleaves long double-stranded RNA (dsRNA) molecules into short fragments of ~20 nucleotides. One of the two strands of each fragment, known as the guide strand, is then incorporated into the RNA-induced silencing complex (RISC). The most well-studied outcome is post-transcriptional gene silencing, which occurs when the guide strand base pairs with a complementary sequence of a messenger RNA molecule and induces cleavage by Argonaute, the catalytic component of the RISC complex. This process is known to spread systemically throughout the organism despite initially limited molar concentrations of siRNA.

The selective and robust effect of RNAi on gene expression makes it a valuable research tool, both in cell culture and in living organisms because synthetic dsRNA introduced into cells can induce suppression of specific genes of interest. RNAi may also be used for large-scale screens that systematically shut down each gene in the cell, which can help identify the components necessary for a particular cellular process or an event such as cell division. Exploitation of the pathway is also a promising tool in biotechnology and medicine.

RNA interference (RNAi) is a post-transcriptional gene-silencing mechanism, by which a specific degradation of mRNA is induced by homologous double-stranded RNAs (dsRNAs), and constitutes a powerful tool for gene function analysis.

RNAi can occur by introducing chemically synthesized siRNA or by endogenous microRNAs (miRNA) that silence cellular mRNAs (miRNAs). Reviewed in Sledz C A, Williams B R. 2005. RNA interference in biology and disease. Blood. 106(3):787-94).

The synthetic dsRNA of 21-23 nucleotides that target a specific region in the mRNA is a synthetic siRNA. Taken advantage of miRNA structure, short hairpin forms (e.g., expressed from shRNA vectors) are about 50-70 nucleotides that comprise sense strand, loop sequences, antisense strand and termination sequence. Once in cells, the hairpins are processed by dicer enzyme into an siRNA that mediates gene silencing. In mammalian cells, the antisense strand of synthetic short interfering RNA (siRNA) serves as a template for the RNA-induced silencing complex (RISC) to recognize and cleave complementary messenger RNA (mRNA), which is then rapidly degraded.

The short inhibitory RNAs (siRNAs) are commonly made as chemically synthesized double-stranded short RNA (19-29 mer) which is relatively easy and has a higher transfection rate. However, it is costly and transient in action. Vector based RNAi approaches included the use of short hairpin RNA (shRNA) as plasmid or virus-based vectors.

The need for inducible (regulated) RNAi vectors allow the precise and temporal control of gene knockdown, to avoid artifactual differences between compared cell populations, reduction of non-specific cellular effects due to induction of transient expression, and for expression of RNAi when extended can cause cellular toxicity or unwanted changes.

The problem is that once RNAi vectors are made, inclusion of regulated sequences, such as tetracycline operator (TetO) sites, require time consuming cloning and use of enzymes, such as restriction enzymes, ligase, topoisomerase, or recombinase. Though the TetO-sites can be synthesized as double stranded polynucleotides or as a PCR product, these still need to be cloned into the vector using restriction sites and cloning enzymes. All of these cloning-based techniques require propagation of the plasmid (including transformation into bacterial cells, culture growth, and plasmid extraction) or the virus-based vector include packaging in cells and virus purification. These cloning-based processes become almost formidable when working with large number of RNAi vectors such as in high-throughput applications.

Thus, there is a need in the art to improve the methods of providing RNAi sequences in an expressable (ready-to-use) format.

There is furthermore a need in the art to improve the methods of providing a (any) gene sequence of interest in an expressable (ready-to-use) format that is simple to handle and/or which furthermore allows assessing post-transcriptional effects.

SUMMARY OF THE INVENTION

The object of the present invention is solved by the subject-matter as defined in the attached claims.

The object of the present invention is particularly solved by a single PCR-based method that simultaneously generates a linear RNA interference expression cassette that is also (TetO-) inducible/repressible.

The object of the present invention is particularly solved by a single PCR-based method that simultaneously generates a linear RNA interference expression cassette that is also inducible/repressible by other systems including but not limited to ecdysone inducible system, a heat shock on/off system, a lacO/IPTG system, a cre system, a cumate repressor protein CymR system, a nitroreductase system, coumermycin/novobiocin-regulated system, a RheoSwitch Ligand RSL1 system, a chimeric bipartite nuclear receptor expression system, a GAL4 system, sterol or steroid or synthetic steroid inducing/repressing system or another inducing/repressing system or an inducing/repressing system hybrid of the above.

In particular, the object of the present invention is solved by providing a method for producing inducible and/or repressible expression active linear RNA interference constructs.

Said method preferably comprises the step of:
(a) generating an inducible/repressible expression active linear RNA interference construct, comprising
 one or more control element(s),
 a minimal promoter,
 an inhibitory RNA coding sequence, and
 a termination sequence,
which step comprises a PCR amplification of a source polynucleotide comprising the inhibitory RNA coding sequence using
 (i) a forward primer comprising
  at its 3' end, a first sequence part complementary to a promoter region of the source polynucleotide upstream of the inhibitory RNA coding sequence, and
  at its 5' end, a second sequence part comprising one or more introduced control element(s); and
 (ii) a reverse primer complementary to a region of the source polynucleotide downstream of the coding region for RNA interference comprising a termination sequence,
or which step comprises a PCR amplification using
 (i) a forward primer comprising
  at its 3' end, a first sequence part complementary to a promoter region of a DNA source, and
  at its 5' end a second sequence part comprising one or more introduced control element(s); and
 (ii) a reverse primer comprising three regions in 3' to 5' direction, namely
  a first region complementary to the 3' end of the promoter region of a DNA source,
  a second region containing the inhibitory RNA coding sequence, and
  a third region containing a termination sequence,
wherein the inhibitory RNA coding sequence is selected from a coding DNA sequence for short hairpin RNA (shRNA), small interfering RNA (siRNA), micro RNA (miRNA) or antisense RNA
wherein the one or more control element(s) are inducible/repressible (on/off) element(s),
wherein step (a) is a single step not involving a cloning step, wherein said cloning step includes the use of restriction digestion, cloning enzyme(s), bacterial transformation and/or plasmid preparation,
wherein expression of the inducible/repressible expression active linear RNA interference construct resulting from (a) is connected with the inducibility of the promoter, which requires the addition of a compound which activates or represses the expression and/or which requires the withdrawal of a compound which represses or activates the expression.

According to the present invention this object is furthermore solved by
 libraries of inducible/repressible expression active linear RNA interference constructs obtained in the method according to the present invention,
 a stable cell line expressing shRNA, siRNA, miRNA or antisense RNA encoded by the inhibitory RNA coding sequence contained in the inducible/repressible expression active linear RNA interference construct obtained in the method according to the present invention,
 a kit for carrying out a method according to the present invention,
 use of the method according to the present invention for producing an array,
 arrays comprising at least two inducible/repressible expression active linear RNA interference constructs obtained in the method according to the present invention in one or more vessels,
 a kit comprising an array comprising at least one of an inducible/repressible expression active linear RNA interference construct obtained in the method according to the present invention.

The object of the present invention is furthermore particularly solved by a single PCR-based method that simultaneously generates a linear gene expression cassette that is also inducible/repressible, such as utilizing the TetO system or any another sequence that causes inducible/repressible expression when linked to an expression cassette.

In particular, the object of the present invention is solved by providing a method for producing inducible and/or repressible expression active linear gene constructs.

Said method preferably comprises the step of:
(a) generating an inducible/repressible expression active linear gene construct, comprising
 one or more control element(s),
 a minimal promoter,
 a DNA sequence selected from a gene, a coding region, an open reading frame (ORF) and a cDNA,
 a 3' untranslated region (3' UTR) containing mRNA destabilization or stabilization elements derived from a 3' UTR of a cellular mRNA, and
 a termination sequence,
which step comprises a PCR amplification of a source expression polynucleotide comprising in 5' to 3' direction a promoter sequence and the DNA sequence using
 (i) a forward primer comprising
  at its 3' end, a first sequence part complementary to a promoter region of the source expression polynucleotide upstream of the DNA sequence, and
  at its 5' end a second sequence part comprising one or more introduced control element(s); and
 (ii) a reverse primer selected from
  a reverse primer complementary to a region of the source expression polynucleotide downstream of the DNA sequence comprising mRNA destabilization or stabilization elements derived from a 3' UTR of a cellular mRNA and a termination sequence, or
  a reverse primer complementary to a region of the source expression polynucleotide downstream of the 3' UTR wherein the region contains mRNA destabilization or stabilization elements of a cellular mRNA with or without a termination sequence,
wherein the source expression polynucleotide is selected from a vector (like an expression vector), a lentivirus, a plasmid, a virus-based vector, or a linear or linearized or amplified fragment thereof,
wherein the minimal promoter is a minimal promoter derived from a transcriptionally non-inducible constitutively active ribosomal protein gene promoter, preferably a minimal promoter derived from a ribosomal protein promoter, more preferably of ribosomal protein S23 (RPS23) and of ribosomal protein S30 (RPS30),
wherein the one or more control element(s) are inducible/repressible (on/off) element(s),
wherein step (a) is a single step not involving a cloning step, wherein said cloning step includes the use of restriction digestion, cloning enzyme(s), bacterial transformation and/or plasmid preparation,
wherein expression of the inducible/repressible expression active linear gene construct resulting from (a) is connected with the inducibility of the promoter, which requires the addition of a compound which activates or represses the expression and/or which requires the withdrawal of a compound which represses or activates the expression.

In a further aspect, said method preferably comprises the step of:
(a) generating an inducible/repressible expression active linear gene construct, comprising
  one or more control element(s),
  a minimal promoter,
  a DNA sequence selected from a gene, a coding region, an open reading frame (ORF) and a cDNA,
  a 3' untranslated region (3' UTR), optionally containing mRNA destabilization or stabilization elements derived from a 3' UTR of a cellular mRNA, and
  a termination sequence,
which step comprises a PCR amplification using the DNA sequence as a template and
  (i) a forward primer comprising three regions in 5' to 3' direction, namely
    a first region containing one or more introduced control element(s),
    a second region containing the minimal promoter,
    a third region that are at or upstream of the initiation codon of the DNA sequence, and
  (ii) a reverse primer complementary to a region at or downstream of the 3' end of the DNA sequence, with or without further comprising a termination sequence, optionally containing mRNA destabilization or stabilization elements derived from a 3' UTR of a cellular mRNA,
wherein the minimal promoter comprises at least a TATA or TATA-like signal,
wherein the one or more control element(s) are inducible/repressible (on/off) element(s),
wherein step (a) is a single step not involving a cloning step, wherein said cloning step includes the use of restriction digestion, cloning enzyme(s), bacterial transformation and/or plasmid preparation,
wherein expression of the inducible/repressible expression active linear gene construct resulting from (a) is connected with the inducibility of the promoter, which requires the addition of a compound which activates or represses the expression and/or which requires the withdrawal of a compound which represses or activates the expression.

According to the present invention this object is furthermore solved by
  uses of the inducible/repressible expression active linear gene construct obtained by a method according to the present invention at conditions that inhibit the expression of the gene or protein for assessing post-transcriptional effects, and/or for identifying compounds that affect post-transcriptional regulation of genes,
  uses of the inducible/repressible expression active linear gene construct obtained by a method according t to the present invention for producing an array,
  arrays produced according to the present invention comprising at least two inducible/repressible expression active linear gene constructs obtained in the method according to the present invention in one or more replicate vessels,
  cells or cell lines harbouring an inducible/repressible expression active linear gene construct obtained in the method according to the present invention, According to the present invention this object is furthermore solved by a method for identifying compounds that affect post-transcriptional regulation of reporter(s) or gene(s).
Said method preferably comprises the following steps
(a) providing at least one inducible/repressible expression active linear gene construct obtained in the method according to the present invention, an array or a stable cell line according to the present invention,
(b) providing at least a compound to be tested,
(c) determining the effect of the compound on the post-transcriptional regulation by determining the mRNA level and/or the expression level of the reporter or gene.

According to the present invention this object is furthermore solved by ac kit for carrying out the above method for identifying compounds that affect post-transcriptional regulation of reporter(s) or gene(s), comprising
(i) at least one inducible/repressible expression active linear gene construct obtained in the method according to the present invention,
(ii) a transfection reagent, and
(iii) an instruction sheet.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

1. Methods for Producing Inducible and/or Repressible Expression Active Linear RNA Interference Constructs First Aspect of the Present Invention)

As outlined above, the present invention provides methods for producing inducible and/or repressible expression active linear RNA interference constructs.

The ease of the methods in converting any RNA inhibitory expressing vector or expressable polynucleotide into TetO or other regulated constructs without virtually any cloning or plasmid preparation step is a remarkable feature of the disclosed invention.

The inducible/repressible expression active linear RNA interference constructs are ready to be used for expressing the RNA interference of interest in cells in a regulatable/regulated manner.

"RNA interference" (RNAi) refers to a post-transcriptional gene-silencing mediated by homologous double-stranded dsRNA inside cells. RNAi can occur by expressing inside cells RNA sequences which specifically target mRNAs of interest. These RNA sequences comprise for example short hairpin RNA (shRNA), small interfering RNA (siRNA), micro RNA (miRNA) or antisense RNA. RNAi can be used for gene silencing, gene knockdown, functional genomics, and therapeutic applications. When cells are exposed to double stranded RNA, which is either formed naturally through miRNA processing pathway or when expressed from an RNAi vector (such as shRNA vector), the dsRNA is then cleaved by a protein called Dicer. This will lead to formation of small 21-23 nucleotide siRNAs which associate with the specific mRNA targeted by their nucleotide sequence in a complex called RISC, which includes RNase activity that degrades the target mRNA. Synthetic siRNA can also be directly transfected into cells to mediate silencing.

Said method comprises the step of:
(a) generating an inducible/repressible expression active linear RNA interference construct, comprising
one or more control element(s),
a minimal promoter,
an inhibitory RNA coding sequence, and
a termination sequence, The inhibitory RNA coding sequence is selected from a coding DNA sequence for short hairpin RNA (shRNA), small interfering RNA (siRNA), micro RNA (miRNA) or antisense RNA.

The one or more control element(s) are inducible/repressible (on/off) element(s), Step (a) is a single step which does not involve a (any) cloning step, wherein said cloning step includes the use of restriction digestion, cloning enzyme(s) as well as plasmid work, including propagation of the plasmid: bacterial transformation (transformation of plasmids into bacterial cells, culture growth) and/or plasmid preparation, plasmid extraction.

Cloning enzymes are e.g. restriction enzymes, ligase, topoisomerase, or recombinase.

Thus, the method does not require time consuming cloning and use of enzymes, for incorporating regulation sequences (such as of the TetO system).

Importantly, the expression of the inducible/repressible expression active linear RNA interference construct resulting from (a) is connected with the inducibility of the promoter.

Wherein the "inducibility" of the promoter requires the addition of a compound which activates/induces or represses the expression and/or which requires the withdrawal of a compound which represses or activates/induces the expression.

In one preferred embodiment of the invention ("top-down" approach), step (a) comprises a PCR amplification of a source polynucleotide comprising the inhibitory RNA coding sequence using
(i) a forward primer comprising
at its 3' end, a first sequence part complementary to a promoter region of the source polynucleotide upstream of the inhibitory RNA coding sequence, and
at its 5' end, a second sequence part comprising one or more introduced control element(s); and
(ii) a reverse primer complementary to a region of the source polynucleotide downstream of the coding region for RNA interference comprising a termination sequence, Preferably, the source polynucleotide—which is used as the template providing the inhibitory RNA coding sequence—a vector (like an expression vector), a lentivirus, a plasmid, a virus-based vector, or a linear or linearized or amplified fragment thereof,
or the source polynucleotide is preferably contained in prokaryotic or eukaryotic cells which contain inhibitory RNA coding sequences selected from sequences coding for shRNA, siRNA, miRNA or antisense RNA sequences.

Preferably, the first sequence part at the 3' end of the forward primer comprises a region of at least 6 nucleotides that binds to a region in the promoter of the source polynucleotide that is at the 5' end or upstream of the inhibitory RNA coding sequence.

In another preferred embodiment of the invention ("bottom-up" approach) step (a) comprises a PCR amplification using
(i) a forward primer comprising
at its 3' end, a first sequence part complementary to a promoter region of a DNA source, and
at its 5' end a second sequence part comprising one or more introduced control element(s); and
(ii) a reverse primer comprising three regions in 3' to 5' direction, namely
a first region complementary to the 3' end of the promoter region of a DNA source,
a second region containing the inhibitory RNA coding sequence, and
a third region containing a termination sequence, Preferably, the DNA source comprises at least a promoter sequence, preferably a minimal promoter.

The DNA source is any polynucleotide construct that harbors/comprises a promoter sequence, preferably a vector (like an expression vector), a lentivirus, a plasmid, a virus-based vector, or a linear or linearized or amplified fragment thereof, or any other DNA sequence comprising the promoter sequence or the minimal promoter sequence from Polymerase I promoter, Polymerase II promoter, and Polymerase III promoter.

The methods for producing inducible and/or repressible expression active linear RNA interference constructs preferably further comprises the following steps:
(b) transfecting a cell or cell line with the inducible/repressible expression active linear RNA interference construct obtained in step (a);
wherein the cell or cell line transiently or stably expresses a repressor system,
(c) expressing shRNA, siRNA, miRNA or antisense RNA encoded by the inhibitory RNA coding sequence contained in the inducible/repressible expression active linear RNA interference construct obtained in step (a),
by the addition of a compound which activates/induces or represses the expression and/or by the withdrawal of a compound which represses or activates/induces the expression;
(d) knocking out the RNA activity which is targeted by the RNA interference construct; and
(e) measuring an expression level or activity of the RNA or protein targeted by the RNA interference construct.

Preferably, the minimal promoter is derived from Pol I promoter, Pol II promoter, Pol III promoter, a synthetic minimal promoter, a viral or cellular promoter.

Pol III promoters are preferably selected from U1 promoter, H1, U6, tRNA, and 7SK.

Pol II promoters are preferably selected from CMV promoter, SV40, LTR, HSV TK, and ribosomal protein promoters.

Pol I promoters are preferably selected from ribosomal RNA promoters.

Preferably, the minimal promoter is a minimal promoter derived from ribosomal protein promoters, preferably of ribosomal protein S23 (RPS23) and of ribosomal protein S30 (RPS30), or from modified ribosomal proteins,
wherein, preferably, the RPS23 promoter or the RPS30 promoter or parts thereof or derivatives thereof are modified for higher expression by modifying the transcriptional initiation sequence, preferably by mutating a TATA-like sequence to the TATA signal sequence, more preferably by substituting the TATA-like signal TACAAATA with the TATA signal TATAAATA.

The termination sequence preferably comprises an eukaroytic polyadenylation signal, pol III termination signal, thymidines stretch, U1 termination signal, pol I termination signal, or synthetic termination variant. Throughout this application, the designation termination shall apply to the above eukaryotic signals in the embodiments.

The inducible/repressible (on/off) element(s) is preferably selected from the group comprising functional sequences of the tetracycline (TetO) on/off system, an ecdysone inducible system, a heat shock on/off system, a lacO/IPTG system, a cre system, a cumate repressor protein CymR system, a nitroreductase system, coumermycin/novobiocin-regulated system, a RheoSwitch Ligand RSL1 system, a chimeric bipartite nuclear receptor expression system, a GAL4 system, sterol or steroid or synthetic steroid inducing/repressing system or another inducing/repressing system or an inducing/repressing system hybrid of the above.

More preferably, the inducible/repressible (on/off) element(s) are functional sequences of the tetracycline (TetO) on/off system.

The repressor system the cell or cell line is transiently or stably expressing (inside the cell) is selected depending on the inducible/repressible (on/off) element(s) of the inducible/repressible expression active linear RNA interference construct.

Also, the compound, which activates or represses the expression of the inhibitory RNA sequence inside the cell or cell line and which has to be added, is selected depending on the repressor system of the cell or cell line and the inducible/repressible (on/off) element(s) of the inducible/repressible expression active linear RNA interference construct,
and/or the compound, which represses or activates the expression of the inhibitory RNA sequence inside the cell or cell line and which has to be withdrawn, is selected depending on the repressor system of the cell or cell line and the inducible/repressible (on/off) element(s) of the inducible/repressible expression active linear RNA interference construct.

It is very preferred to use the TetO system, wherein
the cell or cell line stably or transiently expresses Tet repressor or Tet activator proteins, or their mutant variants,
the inducible/repressible (on/off) element(s) of the inducible/repressible expression active linear RNA interference construct are functional sequences of the tetracycline (TetO) on/off system;
the compound which activates the expression of the inhibitory RNA sequence inside the cell or cell line and which has to be added is selected from tetracyclines, doxycycline, a tetracycline analogue, glycylcycline(s), a modified tetracycline, and synthetic four-ring tetracycline-like structure compounds.

Alternatively, in other systems the compound withdrawal activates the expression of the inhibitory RNA sequences.

Preferably, the inhibitory RNA sequences (which are expressed) are targeted to any gene or mRNA of interest.

In a preferred embodiment, the inducible/repressible expression active linear RNA interference construct is used in animal models.

1.1 Arrays, Libraries, Kits Utilizing the Inducible/Repressible Expression Active Linear RNA Interference Constructs Obtained in the First Method As outlined above, the present invention provides a library of inducible/repressible expression active linear RNA interference constructs obtained in the above method according to the present invention, wherein each construct codes for a different inhibitory RNA sequence.

Preferably, the each construct of the library targets a different gene or mRNA of interest.

As outlined above, the present invention provides a stable cell line expressing shRNA, siRNA, miRNA or antisense RNA encoded by the inhibitory RNA coding (DNA) sequence contained in the inducible/repressible expression active linear RNA interference construct obtained in the above method according to the present invention.

As outlined above, the present invention provides a kit for carrying out the above method according to the present invention.

Said kit preferably comprises a source polynucleotide as defined above for the "top-down" approach or a DNA source as defined above for the "bottom-up" approach, and at least one of the following:
(a) a reverse primer, preferably as defined above,
(b) a forward primer containing inducible/repressible (on/off) element(s), preferably as defined above,
(c) a PCR reagent component,
(d) a transfection reagent, and
(d) an instruction sheet.

As outlined above, the above method according to the present invention can be used for producing an array.

As outlined above, the present invention provides an array comprising at least two inducible/repressible expression active linear RNA interference constructs obtained in the above method according to the present invention in one or more vessels.

Preferably, each vessel contains an inducible/repressible expression active linear RNA interference construct which codes for a different inhibitory RNA sequence targeting a different gene or mRNA of interest An "array" or "microarray" refers to a multiplex technology used in molecular biology and in medicine. It consists of an arrayed series of several, many or even thousands of microscopic spots of molecules/probes (here: the constructs), called features. Typically, the molecules/probes are attached to a solid surface. The solid surface can be glass or a silicon or a plastic chip. Other microarray platforms use microscopic beads, instead of the large solid support. Arrays and microarrays are known in the art. In this application, the arrays and microarrays refer to any formats, including also 96-well plates, 384-well plates, and 1536-well plates, and higher content microarray, etc.

According to the invention, a preferred array platform/format uses vessels or vessel replicates, such as in microtiter plates.

Further these arrays and microarrays may contain the constructs mixed with transfection reagents as transfection-ready format.

As outlined above, the present invention provides a kit comprising an array, preferably a 96-well plate or a 384-well plate, comprising at least one of an inducible/repressible expression active linear RNA interference construct obtained in the above method according to the present invention, and further comprising at least one of the following: (a) a buffer solution for eluting a DNA, (b) a transfection reagent, and (c) a data sheet.

1.2 Preferred Embodiment of the First Aspect of the Invention

In the patent application PCT/EP2008/005278 (which is incorporated herein in its entirety by reference), the inventors developed a method comprising the generation of an expression active linear reporter construct which is controllable or, in other words, regulatable or tunable. This is performed by manipulating the sequence information in the forward primers which contain two regions, a 3' end region that is directed to the vector and can be "vector position-flexible", and a 5' end region that contains cis-acting inducible or repressible elements.

Patent application PCT/EP2008/005278 provides a simpler cloning-free method that utilizes PCR with a specific sequence design of the forward primer along with a universal reverse primer, which will be described in details.

Described therein is a simple cloning-free PCR-based procedure to generate gene and reporter expression cassettes that can be used in many applications in the field of life sciences. This cloning-free approach allows promoter activity assessment or transcriptional manipulations including the use of cis-acting sequences, that otherwise require cloning and time demanding manipulations, particularly in the case of introduced mutations. In particular, a cloning-free approach to generate transcriptionally controllable linear expression active DNA is described. The expression active linear DNA produced by PCR harbors a part of a promoter, a non-inducible or minimal promoter and contains full functional gene or reporter expression cassettes that include the gene or reporter cDNA and 3'UTR. Transcriptional control elements, such as cis-acting elements, or their mutant forms from several bases to 140 or 200 bases are simply appended to a common DNA sequence in a forward PCR primer that targets the upstream region of the gene or reporter gene of choice, such as reporters, by a single PCR or more, if required. With two- and three-step PCRs, one can generate a 400 bases promoter or transcriptional regulatory elements, if required. The forward 5' upstream primer is versatile in its nucleotide composition, any transcriptional element or regulatory element can be added including mutations and polymorphisms. The described regulated linear reporter gene approach, i.e. introducing a transcriptional control in the linear gene PCR product is simple, versatile and adaptable to high throughput studies that are important in both academic and pharmaceutical research and development activities including drug discovery processes. The invention can be used with any different applications in the field of life sciences including, but not limited to, drug screening, drug target screening, research tool in molecular and cell biology, personalized medicine, pharmacogenomics, and correlation of genetic variations and polymorphisms with phenotypic outcomes.

The principal advantage of the invention disclosed in International patent application PCT/EP2008/005278 is the ease of introducing a transcriptional control of gene or reporter construction, ease of sequence manipulations such as mutations and deletions, reliability, and adaptability to large scale experiments and high throughput drug screening. The assay is dependent on amplification of a functional reporter expression cassette from an optimized mammalian expression vector that is efficient when transfected as PCR product to express the protein of interest. The desired promoter sequences such as a minimal promoter with or without wild type and mutant cis-acting sequences are included in the forward primer that contains at the 5' end several nucleotides targeting a common region upstream of the gene or reporter cDNA. The sequences in the forward primer binding to a common region in the vector or source DNA can be as little as 6 nucleotides. The preferred length is more than 10 bases, particularly preferred is more than 12 bases. The source DNA which can be used for amplification can be the vector itself, a linearized vector that contains the whole functional gene product or reporter cassette, or a linear DNA generated by PCR that contains the whole functional gene product or reporter.

The inventor has used that invention with several different strategies. All of the assays employ a universal reverse primer that target the vector DNA downstream of 3' UTR and a forward primer that targets a region upstream of the reporter construct, depending on the application. In all of the strategies, each PCR is used with one forward and one universal reverse primer. The reverse primer is a universal primer that targets a region downstream of a polyA signal that is sufficient for optimal expression. The preferred distance from the polyA signal is at least 5 nucleotides, particularly preferred is more than 13 bases, and more preferred is more than 20 bases. The specific sequences in the universal primer binding to a vector or source DNA can be as little as 6 nucleotides. The preferred length is more than 10 bases, particularly preferred is more than 14 bases.

The assay is dependent on amplification of a functional gene product including a reporter expression cassette from an expression vector or DNA source that, when transfected as a linear product, is efficient to express the reporter (FIG. 1). The DNA source can be an expression vector or a fragment of the expression vector. The fragment of the expression vector should harbor the expression cassette composed of a promoter, a cDNA of the gene of interest, and a polyA signal. The vector or plasmid can be produced in abundant amounts using bacterial cultures. The fragment can be linearized by restriction fragments flanking this expression cassette. Alternatively, the expression cassette can be produced by PCR with primers flanking the expression cassette.

The primary goal of the invention of International patent application PCT/EP2008/005278 was to provide a simple method for producing transcriptional control elements and transcriptional manipulations of a reporter gene as linear DNA constructs for "in vivo" applications, i.e., using assays based on living cells. Specifically, the present invention's aim is to provide a simple method for manipulating promoter and transcriptional control and regulatory elements including introduced mutations and genetic variations, without the need for the time-demanding cloning steps. The method is also useful for identifying and analyzing new cis- and trans-acting regulatory sequences/factors as well as is particularly useful for drug screening and drug discovery.

The assessment and measurement of the reporter activity can be approaches, not only of the activity of the reporter proteins, but also of the levels of the reporter proteins. Reporter levels, whether intracellular or secreted, can be measured by any detection method including Western blotting, colorimetric method, fluorescence, luminescence, biosensors, and many others. Also, mRNA levels of the reporter can be used to monitor the transcription of the promoter. The mRNA levels can be assessed and quantified by a variety of techniques including, but not limited to, semi-quantitative PCR, real-time PCR, Northern blotting, RNase protection assay, beads-dependent mRNA quantification, in situ hybridization, and others. Examples of fluorescence, luminescence, and mRNA levels are disclosed in International patent application PCT/EP2008/005278.

Because of the ease of producing the linear reporter and introducing desired variations leading to the transcriptional control, one may expect to produce a high throughput array composed of these linear reporters harboring the different transcriptional control elements and their variations such as mutations. Nowadays, there are many high-throughput automation systems that facilitate the process including cell dispensing, transfection, and detection systems. Detection systems such as imaging of fluorescent reporters are those such as the automated imagers available from BD imaging systems (BD Dickinson, Inc.), Genetix, and Cellomics. Microplate readers and array scanners can also be applied in high throughput applications.

Thus, the method allows a versatile number of applications including, but not limited to, making a library of transcriptionally regulated functional linear reporter or gene PCR products, an array containing functional linear reporter PCR products in which each of the array feature contains a transcriptional factor or regulatory element, and a kit that contains the necessary reagents to construct the linear reporter PCR product.

Versatility of reporter systems allows use in many applications, for example, but not limited to, drug discovery, drug target discovery, bioassay development, bioassays, cytokine bioassays, interferon response bioassays, virus response bioassays, metal response bioassays, stress response bioassay, inflammatory response bioassays, cell growth assay, cellular behavior indicator assays, angiogenesis bioassay, chemotaxis and metastasis assays, hypoxia assays, environmental changes bioassays using parameters, such as heat, nutrient, radiation, oxygen, pH, salts, toxins. Additionally, any bioassay for inhibition of above responses is also a potential application.

In the present invention, the inventors are utilizing the method of PCT/EP2008/005278 for the preferred embodiment of RNAi.

In the present invention, two important facts underlying inventive step are directed at the source polynucleotide: (a) it harbours an inhibitory RNA coding sequence, and (b) linked to any promoter or fragment from e.g. Pol III and Pol I promoters.

"RNA interference" (RNAi) is a post-transcriptional gene-silencing mediated by homologous double-stranded dsRNA. RNAi can occur by introducing chemically synthesized siRNA or by endogenous microRNAs (miRNA) that silence cellular mRNAs (miRNAs), reviewed in (Sledz C A, Williams B R. 2005. RNA interference in biology and disease. Blood. 106(3):787-94). The synthetic dsRNA of 21-23 nucleotides that target a specific region in the mRNA is a synthetic siRNA. Taken advantage of miRNA structure, short hairpin forms (e.g., expressed from shRNA vectors) are about 50-70 nucleotides that comprise sense strand, loop sequences, anti-sense strand and termination sequence. Once in cells, there hairpins are processed by dicer enzyme into an siRNA that mediates gene silencing. In mammalian cells, the antisense strand of synthetic short interfering RNA (siRNA) serves as a template for the RNA-induced silencing complex (RISC) to recognize and cleave complementary messenger RNA (mRNA), which is then rapidly degraded.

Commercially available shRNA vectors express shRNA under control of the U1 promoter. The U1 promoter is a polymerase II (Pol II) type promoter which have been used customarily for shRNA vectors. Among other useful Pol II promoters are H1, U6, tRNA, and 7SK. Also, both Pol II and Pol I promoters such as CMV promoter and ribosomal RNA promoters. The shRNA RNA vector can harbor also selection marker such hygromycin, neomycin, blasticidine or puromycin resistance gene or fluorescent markers, such as GFP, for selection of transfected cells. Any other structure of the inhibitory RNA can be used for example as miRNA based sequence. Usually shRNA consists of sense strand, loop sequence, anti-sense RNA, and termination, so that we expressed it forms a hairpin structure.

In order to convert the shRNA vector into TetO-inducible form, the shRNA vector was used as source DNA/source polynucleotide for amplification (FIG. 1). The amplified cassette includes a minimal region of the promoter that drives the expression of shRNA with incorporated TetO sequences. The incorporation of the TetO sequences was made possible by the inclusion of TetO sequence in the 5'end of the forward primer. The forward primers also has several nucleotides at the 3'end to target the desired region of the promoter The reverse primer target a region downstream of the shRNA to allow amplification of the region and inclusion of the termination sequences. The TetO sequence or its variants can be incorporated as one, two, or more copies in the forward primer.

Preferred TetO sequences are

| | |
|---|---|
| ATCCCTATCAGTGATAGA | SEQ ID NO. 9 |
| TCCCTATCAGTGATAGAGA | SEQ ID NO. 10 |
| CTATCAGTGATAGAGA | SEQ ID NO. 11 |
| TCAGTGATAGAGA or minimally | SEQ ID NO. 12 |
| TGATAG | SEQ ID NO. 13 |
| ACTCTATCATTGATAGAGT | SEQ ID NO. 14 | or their variants or truncated variants.

The tetO-regulated system is only an example of regulated sequences that can be used. Although, tetO-based method is a preferred embodiment and one of the most studied system and has been adopted in many several commercial vectors by cloning techniques (Gossen, M., and Bujard, H. (2002). Studying gene function in eukaryotes by conditional gene inactivation. Annual review of genetics 36, 153-173; U.S. Pat. No. 6,133,027). The embodiments are not limited to tetO but including the following but not limited to: ecdysone inducible system, heat shock on/off system, lacO/IPTG system, cre system, cumate repressor protein CymR system, a RheoSwitch Ligand RSL1 system, coumermycin/novobiocin-regulated system, a chimeric bipartite nuclear receptor expression system, GAL4 system, nitroreductase, sterol or steroid or synthetic steroid inducing/repressing system.

Throughout the present application, the TetO sequences/system can be considered as cis-acting inducible/repressible sequences.

The method calls for converting any RNAi/shRNA vector into inducible RNAi/shRNA construct by a single PCR step without the use of plasmid-involving cloning steps or cloning enzymes, such as restriction digestion, ligase reaction, recombination, topoisomerase reaction. wherein step (a) is a single step not involving cloning steps, wherein said cloning steps include the use of restriction digestion, cloning enzymes and plasmid work.

Once the TetO-inducible RNAi/shRNA cassette is produced, it is ready to transfect desired cells. Any transfection and delivery method known in the art can be used. In Tet-on system, in the presence of doxycycline or other tetracycline analogue, the reverse tetracycline rtTA transactivator is active and binds to TetO-linked shRNA promoter activating the transcription of the shRNA resulting in knockdown of the target mRNA. In the Tet-off system, in the presence of doxycycline or tetracycline analogue, the tetracycline-controlled transactivator (tTA) is unable to bind TetO sequences and transcription is shut-off.

In tetOn-system, the shRNA is activated when induced by the tetracycline analogues, and thus, shRNA is able to knockdown the target mRNA. In Tet-off system, the shRNA is not transcribed and thus mRNA knockdown is not taking place.

2. Methods for Producing Inducible and/or Repressible Expression Active Linear Gene Constructs (Second Aspect of the Present Invention)

As outlined above, the present invention provides methods for producing i inducible and/or repressible expression active linear gene constructs.

The ease of the methods in converting any gene expression vector or expressable polynucleotide into TetO or other regulated constructs without virtually any cloning or plasmid preparation step is a remarkable feature of the disclosed invention.

The inducible/repressible expression active linear gene constructs are ready to be used for expressing the gene/encoded protein of interest in cells in a regulatable/regulated manner.

"Top-Down Approach"

In this preferred embodiment, step (a) uses as template a a source expression polynucleotide comprising in 5' to 3' direction a promoter sequence and the DNA sequence of interest.

Said method comprises the step of:
(a) generating an inducible/repressible expression active linear gene construct, comprising
  one or more control element(s),
  a minimal promoter,
  a DNA sequence selected from a gene, a coding region, an open reading frame (ORF) and a cDNA,
  a 3' untranslated region (3' UTR) containing mRNA destabilization or stabilization elements derived from a 3' UTR of a cellular mRNA, and
  a termination sequence.

The step comprises a PCR amplification of a source expression polynucleotide comprising in 5' to 3' direction a promoter sequence and the DNA sequence using
(i) a forward primer comprising
  at its 3' end, a first sequence part complementary to a promoter region of the source expression polynucleotide upstream of the DNA sequence, and
  at its 5' end a second sequence part comprising one or more introduced control element(s); and
(ii) a reverse primer selected from
  a reverse primer complementary to a region of the source expression polynucleotide downstream of the DNA sequence comprising mRNA destabilization or stabilization elements derived from a 3' UTR of a cellular mRNA and a termination sequence, or
  a reverse primer complementary to a region of the source expression polynucleotide downstream of the 3' UTR wherein the region contains mRNA destabilization or stabilization elements of a cellular mRNA with or without a termination sequence, The source expression polynucleotide—which is used as the template providing the DNA sequence and the promoter sequence—is selected from a vector (like an expression vector), a lentivirus, a plasmid, a virus-based vector, or a linear or linearized or amplified fragment thereof, The minimal promoter is a minimal promoter derived from a transcriptionally non-inducible constitutively active ribosomal protein gene promoter, preferably a minimal promoter derived from a ribosomal protein promoter, more preferably of ribosomal protein S23 (RPS23) and of ribosomal protein S30 (RPS30).

The one or more control element(s) are inducible/repressible (on/off) element(s), Importantly, step (a) is a single step which does not involve a (any) cloning step, wherein said cloning step includes the use of restriction digestion, cloning enzyme(s) as well as plasmid work, including propagation of the plasmid: bacterial transformation (transformation of plasmids into bacterial cells, culture growth) and/or plasmid preparation, plasmid extraction.

Cloning enzymes are e.g. restriction enzymes, ligase, topoisomerase, or recombinase.

Thus, the method does not require time consuming cloning and use of enzymes, for incorporating regulation sequences (such as of the TetO system).

The expression of the inducible/repressible expression active linear gene construct resulting from (a) is connected with the inducibility of the promoter.

Wherein the "inducibility" of the promoter requires the addition of a compound which activates/induces or represses the expression and/or which requires the withdrawal of a compound which represses or activates/induces the expression.

Preferably, the RPS23 promoter or the RPS30 promoter or parts thereof or derivatives thereof are modified for higher expression by modifying the transcriptional initiation sequence, preferably by mutating a TATA-like sequence to the TATA signal sequence, more preferably by substituting the TATA-like signal TACAAATA with the TATA signal TATAAATA.

Preferably the minimal promoter further comprises at least one sp1 site-containing sequence, preferably obtained by truncating the RPS23 promoter or the RPS30 promoter and adding at least one sp1 site-containing sequence.

Preferably, the minimal promoter further comprises
  intron sequence(s) of ribosomal proteins, preferably of RPS30 and/or RPS23, or parts thereof,
  exon sequence(s) of ribosomal proteins, preferably of RPS30 and/or RPS23, or parts thereof,
  modified sequences wherein the modification eliminates a restriction site.

Preferably, the minimal promoter comprises a nucleic acid sequence of any of SEQ ID NOs. 3 to 8 or a sequence complementary thereof.

Preferably, the forward primer comprises a nucleic acid sequence selected from of SEQ ID NOs. 13 or 14.

"Bottom-Up" Approach

In this other preferred embodiment, step (a) uses as template the DNA sequence of interest (such as a gene, a coding region, an open reading frame (ORF) or a cDNA) of interest, which:
  is not comprised in an expression plasmid or expression vector (it is e.g. "naked" cDNA),
  does not comprise a promoter sequence.

In this embodiment, the method for producing inducible and/or repressible expression active linear gene constructs, comprises the step of:

(a) generating an inducible/repressible expression active linear gene construct, comprising
  one or more control element(s),
  a minimal promoter,
  a DNA sequence selected from a gene, a coding region, an open reading frame (ORF) and a cDNA,
  a 3' untranslated region (3' UTR) optionally containing mRNA destabilization or stabilization elements derived from a 3' UTR of a cellular mRNA, and
  a termination sequence,
which step comprises a PCR amplification using the DNA sequence as a template and
  (i) a forward primer comprising three regions in 5' to 3' direction, namely
    a first region containing one or more introduced control element(s),
    a second region containing the minimal promoter,
    a third region that are at or upstream of the initiation codon of the DNA sequence, and
  (ii) a reverse primer complementary to a region at or downstream of the 3' end of the DNA sequence, with or without further comprising a termination sequence, optionally containing mRNA destabilization or stabilization elements derived from a 3' UTR of a cellular mRNA.

The minimal promoter comprises at least a TATA or TATA-like signal.

The one or more control element(s) are inducible/repressible (on/off) element(s).

Importantly, step (a) is a single step which does not involve a (any) cloning step, wherein said cloning step includes the use of restriction digestion, cloning enzyme(s) as well as plasmid work, including propagation of the plasmid: bacterial transformation (transformation of plasmids into bacterial cells, culture growth) and/or plasmid preparation, plasmid extraction.

Cloning enzymes are e.g. restriction enzymes, ligase, topoisomerase, or recombinase.

Thus, the method does not require time consuming cloning and use of enzymes, for incorporating regulation sequences (such as of the TetO system).

The expression of the inducible/repressible expression active linear gene construct resulting from (a) is connected with the inducibility of the promoter.

Wherein the "inducibility" of the promoter requires the addition of a compound which activates/induces or represses the expression and/or which requires the withdrawal of a compound which represses or activates/induces the expression.

This particular embodiment is preferably to convert a non-expressible DNA sequence (such as cDNA, for example from a cDNA library) that lacks a promoter, into an linear product, that can be expressed and that is also regulatable/regulated (such as TetO-regulated).

Preferably, the forward primer comprises one or more regulatory sequence element(s) or transcriptional element(s), preferably selected from transcriptional enhancing or translational enhancing element(s), such as Kozak sequence(s).

The methods for producing inducible and/or repressible expression active linear gene constructs (both the top-down and the bottom-up approach) preferably further comprise the following steps:
(b) transfecting a cell or cell line with the inducible/repressible expression active linear gene construct obtained in step (a);
wherein the cell or cell line transiently or stably expresses a repressor system, (c) expressing the protein encoded by the DNA sequence contained in the inducible/repressible expression active linear gene construct obtained in step (a)
by the addition of a compound which activates/induces or represses the expression and/or by the withdrawal of a compound which represses or activates/induces the expression; and
(d) measuring gene expression level or activity of the protein expressed in step (c).

The termination sequence preferably comprises an eukaroytic polyadenylation signal, pol III termination signal, thymidines stretch, U1 termination signal, pol I termination signal, or synthetic termination variant. Throughout this application, the designation termination shall apply to the above eukaryotic signals in the embodiments.

Preferably, the inducible/repressible (on/off) expression elements is selected from the group comprising functional sequences of the tetracycline (TetO) on/off system, an ecdysone inducible system, a heat shock on/off system, a lacO/IPTG system, a cre system, a cumate repressor protein CymR system, a nitroreductase system, coumermycin/novobiocin-regulated system, a RheoSwitch Ligand RSL1 system, a chimeric bipartite nuclear receptor expression system, a GAL4 system, sterol or steroid or synthetic steroid inducing/repressing system or any inducing/repressing system or hybrid system.

More preferably, the inducible/repressible (on/off) expression elements are one or more, more preferably two to three, functional sequences of the tetracycline (TetO) on/off system, such as the TetO sequence of SEQ ID NOs. 9 to 14.

An embodiment is the use of the CpG island containing sequences as inducible/repressible (on/off) expression elements to study promoter methylation activities inside cells. This embodiment can be used with any gene but preferably with a reporter. In this case, preferably, the gene or reporter is fluorescent reporter, green fluorescent protein (GFP) and derivatives, enhanced green fluorescent protein (EGFP) and derivatives, luciferase, modified luciferase, inhibitory RNA coding sequence, secreted reporter forms, alkaline phosphatase, CAT, β-galactosidase, antibody, immunoglobin fragment, cDNA fragment, and domain sequences.

The CpG islands are important in promoter function, when methylated, promoter activity is reduced. Thus, any sequence harboring CpG island and their mutants can be used to construct methylation promoter reporter system without cloning using a reporter gene. As an example, the cAMP response element TTACGTCA [SEQ ID NO. 31] and its mutant TTATGTCA-linked reporter construct [SEQ ID NO. 32] is methylated or unmethylated in cancer cells.

Preferably, the DNA sequence encodes a gene which is selected from a group comprising: reporter, fluorescent reporter, green fluorescent protein (GFP) and derivatives, enhanced green fluorescent protein (EGFP) and derivatives, luciferase, modified luciferase, inhibitory RNA coding sequence, secreted reporter forms, alkaline phosphatase, CAT, β-galactosidase, antibody, immunoglobin fragment, cDNA fragment, open reading frame (ORF) and domain sequences.

In a preferred embodiment, the DNA sequence encodes an inhibitory RNA coding (DNA) sequence, which is selected from a coding DNA sequence for short hairpin RNA (shRNA), small interfering RNA (siRNA), micro RNA (miRNA) or antisense RNA.

It is preferred that the mRNA destabilization elements are selected from AU-rich elements, GU-rich elements, or U-rich sequences or other repeats or dinucleotides known to affect mRNA stability.

It is preferred that the mRNA stabilization elements are selected from GC-rich elements, CU-rich elements, or UG-rich sequences, or other repeats or dinucleotides known to affect mRNA stability.

Preferably, the repressor system the cell or cell line is transiently or stably expressing is selected depending on the inducible/repressible (on/off) element(s) of the inducible/repressible expression active linear RNA interference construct.

Also, the compound, which activates or represses the expression of the gene or protein inside the cell or cell line and which has to be added, is selected depending on the repressor system of the cell or cell line and the inducible/repressible (on/off) element(s) of the inducible/repressible expression active linear gene construct, and/or the compound, which represses or activates the expression of the gene or protein inside the cell or cell line and which has to be withdrawn, is selected depending on the repressor system of the cell or cell line and the inducible/repressible (on/off) element(s) of the inducible/repressible expression active linear gene construct.

2.1 Arrays, Libraries, Kits and Methods Utilizing the Inducible/Repressible Expression Active Linear Gene Constructs Obtained in the Second Method As outlined above, the present invention provides the use of the inducible/repressible expression active linear gene construct obtained by the above method according to the present invention at conditions that inhibit the expression of the gene or protein for assessing post-transcriptional effects.

As outlined above, the present invention further provides the use of the inducible/repressible expression active linear gene construct obtained by the above method according to the present invention for identifying compounds that affect post-transcriptional regulation of genes.

The present invention further provides the use of the inducible/repressible expression active linear gene constructs obtained by the above method according to the present for producing an array.

The array produced according to the present invention comprises at least two inducible/repressible expression active linear gene constructs obtained in the above method according to the present invention in one or more replicate vessels.

Preferably, each vessel contains an inducible/repressible expression active linear gene construct with a different 3'UTR or post-transcriptional control element(s).

An "array" or "microarray" refers to a multiplex technology used in molecular biology and in medicine. It consists of an arrayed series of several, many or even thousands of microscopic spots of molecules/probes (here: the constructs), called features. Typically, the molecules/probes are attached to a solid surface. The solid surface can be glass or a silicon or a plastic chip. Other microarray platforms use microscopic beads, instead of the large solid support. Arrays and microarrays are known in the art. In this application, the arrays and microarrays refer to any formats, including also 96-well plates, 384-well plates, and 1536-well plates, and higher content microarray, etc.

According to the invention, a preferred array platform/format uses vessels or vessel replicates, such as in microtiter plates.

Further these arrays and microarrays may contain the constructs mixed with transfection reagents as transfection-ready format.

The present invention further provides a cell or cell line harbouring an inducible/repressible expression active linear gene construct obtained in the method according to the present invention, preferably expressing a reporter or gene protein from the construct, wherein the cell line is preferably a stable cell line.

Furthermore, the present invention further provides a method for identifying compounds that affect post-transcriptional regulation of reporter(s) or gene(s).

Said method comprises the following steps
(a) providing at least one inducible/repressible expression active linear gene construct obtained in the method according to the present invention, an array or a stable cell line according to the present invention,
(b) providing at least a compound to be tested,
(c) determining the effect of the compound on the post-transcriptional regulation by determining the mRNA level and/or the expression level of the reporter or gene.

Furthermore, the present invention further provides a kit for carrying out the method for identifying compounds that affect post-transcriptional regulation of reporter(s) or gene(s).

Said kit preferably comprises
(i) at least one inducible/repressible expression active linear gene construct obtained in the method according to the present invention,
(ii) a transfection reagent, and
(iii) an instruction sheet.

2.2 Minimal Ribosomal Promoters

As described in the application PCT/EP2008/009712 (which is incorporated herein in its entirety by reference), the inventors developed expression vectors derived from ribosomal protein 23 (RPS23) and ribosomal protein 30 (RPS30) that are transcriptionally non-inducible and constitutively active. Thus, the expression vectors are highly suitable for a number of applications, particularly for selective post-transcriptional assessment. Generally, these ribosomal protein promoters lead to weak expression levels, but, in that patent application, RPS23 and RPS30 were rendered for moderate expression. Unlike CMV and SV40 promoters, the modified RPS30IM system (wherein RPS30IM system refers to RPS30I-M1, RPS30I-M2, RPS30I-M2T, RPS30I-M1TOD as well as RPS30I-M1TOU, see below) was not activated by a number of stimuli and inducers. For example, the RPS30I-M1 system was applied to investigate responses to TNF-α or IL-α in the presence of the phosphatase inhibitor, okadaic acid, known to stabilize AU-rich elements containing-mRNAs and was found to be responsive in a manner that is independent on transcriptional induction. For more details, see herein below, and Figures and Examples.

RPS23 and RPS30 and their variants (see earlier application PCT/EP2008/009712) are non-inducible cellular ribosomal promoters that can be suitable for controlled transcriptional inducibility and/or for post-transcriptional assessment. FIG. 4 shows the utility of the RPS promoters and their linked polynucleotides including but not limited to cDNA, ORF, gene fragment, inhibitory RNA such as siRNA, miRNA, and shRNA coding sequences, and reporter genes. The RPS expression cassette can be used as source expression polynucleotide to generate inducible/repressible (On/Off), such as Tet-On or Tet-Off system, expression active linear gene constructs.

Preferred ribosomal protein gene promoters of the invention are the promoter of ribosomal protein S23 (RPS23) and ribosomal protein S30 (RPS30), more preferably the human RPS23 promoter or human RPS30 promoter.

The sequences of RPS23 and RPS30 can be found in the RPG ribosomal protein gene database (http://ribosome.miyazaki-med.ac.jp). See also SEQ ID NOs. 1 and 2.

The gene of Homo sapiens RPS30 or RPS23, respectively, contain several intron and exon sequence sections as well as a 5' upstream and a 3' downstream region, wherein the promoter region is in the 5' upstream region.

Furthermore preferred are sequences that can be derived from the preferred ribosomal protein gene promoters.

Furthermore, parts or partial sequences of the preferred ribosomal protein gene promoters are also preferred, such as truncated sequences of these promoters, e.g. 5' truncated sequences.

Preferably, truncated sequences that have a length of at least about 25 nucleotides are preferred, such as truncated sequences that have a length of about 50, 100, 150, 200, 250, 300, 350, 400 nucleotides.

In other words, the truncation is of at least 25 nucleotides or about 50 or 100 nucleotides, wherein the 5' truncation is preferred. The truncation can also be of 500, 550, 600 or more nucleotides.

Thus, truncations are preferred in a range from about 100 to 1000 nucleotides including all individual integers within that range, wherein the truncation depends on the length of the wildtype or starting sequence. The term "including all individual integers within that range", when used in relation to a range, means, for example, and when e.g. the range is 100 to 500: 100, 101, 102, 103, ( . . . ) 496, 497, 498, 500.

For example, RPS30-M1 (SEQ ID NO. 3) is 5'-truncated promoter in which 600 bases were deleted from the 5'end of the wild type promoter sequence (SEQ ID NO. 1); RPS30-M2 (SEQ ID NO. 4) is 5'-truncated promoter in which 535 bases were removed from the wild type sequence of SEQ ID NO1.

The inventors have found that these preferred promoters or parts thereof can be modified for higher expression.

The modifications are mutations, deletions, substitutions of single or several nucleotides, insertion/including of nucleic acid sequences.

The following modifications are preferred:
modifying the transcriptional initiation sequence,
preferably by mutating a TATA-like sequence to the TATA signal sequence,
more preferably by substituting the TATA-like signal TACAAATA with the TATA signal TATAAATA,
including at least one sp1 site-containing sequence,
preferably obtained by truncating the RPS23 promoter or the RPS30 promoter and adding at least one sp1 site-containing sequence.

In preferred embodiments, two, three, four or more sp1 site-containing sequences are included. Sp1 sites are known in the art. Examples are given herein.

For example,
RPS30-M1 (SEQ ID NO. 3), which is a 5'-truncated promoter in which 600 bases were deleted from the 5'end of the wild type promoter sequence (SEQ ID NO. 1), has two sp1 sites: TCCCGCCCCGTCCTGCG (position: 230-250 of SEQ ID NO. 3) and GGGGCGGAGC (position: 290-300 of SEQ ID NO. 3).
RPS30-M2 (SEQ ID NO. 4) is a 5'-truncated promoter in which 535 bases were removed from the wild type sequence of SEQ ID NO1. A 100 bases (position of wild type) that contain additional sp1 site was added: (position of 4-21 of SEQ ID NO. 4 GCCGGGCA TGGTG-GCGGG) and (position: 75-87 of SEQ ID NO. 4 GGGAGGC GGAGC). In addition to the following sp1 sites: TCCCGCCCCGTCCTGCG (position: 281-297 of SEQ ID NO. 4) and GGGGCGGAGC (position: 340-49 of SEQ ID NO. 4). Thus, RPS30-M2 contains 4 sp1 sites.

The above modifications can also be combined.

The promoter region (a) furthermore preferably comprises one or several of the following
intron sequence(s) of ribosomal proteins, preferably of RPS30 and/or RPS 23, or parts thereof,
preferably first intron of RPS30 (intron 1 of RPS30) or first intron of RPS23 (intron 1 of RPS23)

The intron sequences act primarily to enhance mRNA accumulation; spliced mRNAs also exhibit higher translational yields than intron-less transcripts.
exon sequence(s) of ribosomal proteins, preferably of RPS30 and/or RPS 23, or parts thereof,
preferably exon 1 of RPS30 or exon 1 of RPS23
or a part of exon 2 of RPS23 for splicing, such as the first nine nucleotides of exon 2 of RPS23,
modified sequences wherein the modification eliminates a restriction site.
such as
a BamH1 site CACTGAG can be eliminated by mutating it into CACCTTGAG,
a ATG can be eliminated by mutating it into CTG.

The expression vectors according to the present invention preferably comprise a nucleic acid sequence of any of SEQ ID NOs. 3 to 8 or a sequence complementary thereof
2.3 3' Untranslated Regions (3' UTR)

The 3' UTR of the constructs preferably comprises or contains mRNA destabilization or stabilization elements which are derived from a 3' UTR of a cellular mRNA.

Post-transcriptional regulation can be mediated by 3' UTR that harbor mRNA destabilization elements such as AU-rich elements (for a review see Khabar and Young, 2007). Any sequence fragment of 3'UTR can be used which contains sequence elements that negatively or positively affect the post-transcriptional outcome, i.e., at mRNA or protein levels.

mRNA destabilization or stabilization elements are preferably selected from AU-rich elements, GU-rich elements, or U-rich sequences or any other repeat sequences.
2.4 TetO System TetO is the tetracycline-resistance operon (TetO) and the TetO-based system is regulated by the repressor, rtTA, or the activator protein, tTA, the Tet-On and Tet-Off systems (Ref: Gossen M, Bujard H: Studying gene function in eukaryotes by conditional gene inactivation. Annual review of genetics 2002, 36:153-173.). The problem is that construction of TetO system requires cloning of the TetO upstream or downstream of the TATA box of a reporter or other gene product, cloning including, but not limited to use of enzymes such as restriction enzyme, topoisomearse, recombinase, and ligase and plasmid propagation is costly and time consuming particularly with high-throughput applications.
2.5 Preferred Embodiments of the Second Aspect of the Invention Linear constructs were generated by PCR that contains any where from one to more TetO copies, preferably two to three, since these are incorporated in the forward primer, and minimal ribosomal protein promoter arrangements (FIG. 4).

The design of the forward primer, through 3'end sequence, allows flexibility in choosing the minimal sequences of the ribosomal protein promoter. The targeted regions that are used as examples were either −24 or −68 bases upstream the TATA box of the RPS23 or RPS30. These promoters were modified to include TATA box as they are TATA-less (see earlier application K30346PCT) DNA. The 5'end part allows inclusion of two or more copies of the TetO (SEQ 12 and 13).

The reverse primer targets a region downstream of the polyA to complete the expression active PCR product.

The PCR products are transfected into a HeLa-Tet off cell line that constitutively expresses the transactivator, tTA. In the presence of the tetracycline analog, doxycycline, tTA is inactive. In the absence of doxycycline, the tTA is active, and binds TetO containing promoter and thereby activates transcription of the linked gene.

The TetO$_3$-minimal promoter (−24) containing construct had better suppression in the presence of doxycycline (~87%) when compared to the construct with extended (−68) minimal promoter (FIG. 5). Doxycycline has no effect on EGFP linear control constructs that lack TetO sequences.

In Tet-On system, the cells stably express the rtTA transactivator that is unable to bind TetO sequences in absence of doxycycline, when doxycycline is added, it activates the TetO-linked promoter.

We have used both Tet-On Hek293 and Tet-Off Hela 293 (FIG. 6). The −24 TetO3-linked PCR products were transfected into the cells. The −24 construct led to 77 fold induction of the linked gene in HEK293 with minimal leakage in absence of doxycycline whereas −68 construct led to more leakage and lower induction (6-fold). Whereas, in HeLa Tet-On the −24 construct did not lead to significant induction but with the −68 construct, 13 fold induction was achieved (FIG. 6).

The following drawings and examples illustrate the present invention without, however, limiting the same thereto.

A shRNA expression plasmid harboring shRNA that targets a gene of interest is used as a template for PCR. Forward primer contains 3' end sequences that can flexibly target a region in a promoter in the vector template to allow, minimal promoter activity and 5' end sequences that contain two or three copies of TetO sites. The reverse universal primer targets a region downstream of termination site. Once transfected in a cell line that expresses the repressor that is activated when doxycycline binds to, the shRNA is transcribed and inhibits the gene activity.

FIG. 2

TetOn-HEK293 cell line was seeded in 96-well microplate at 3×10$^3$ cell per well overnight. The cells were transfected with the TetO-regulated shRNA expressing PCR products that were obtained by converting the shRNA vector into TetO-inducible/repressible linear cassette by a single PCR method. The cells were also co-transfected with the target gene, HuR-GFP expressing plasmid (25 ng each well). Transfection was performed with lipofectinamine 2000 (Invitrogen, U.S.). After 24 hrs, the HuR protein levels were quantitated using the fluorescence output generated from the HuR-GFP fusion protein.

Figure 3:
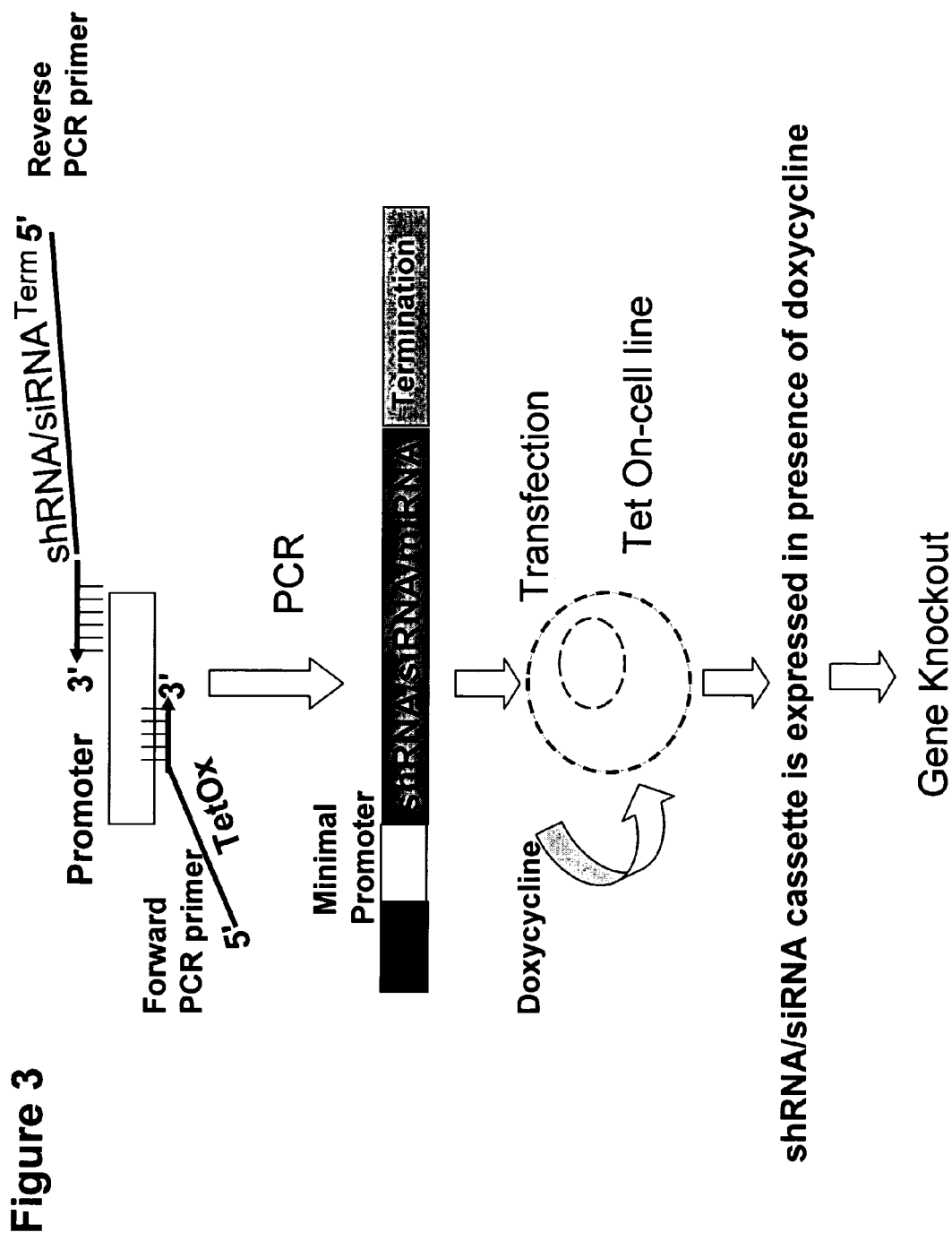

FIG. 3 Schematic representation of generation and production of tetracycline-inducible shRNA linear construct without cloning ("bottom-up method").

A source polynucleotide that harbors a promoter or minimal promoter is used for PCR. Forward primer contains 3' end sequences that can flexibly target a region in a promoter in the source polynucleotide template to allow minimal promoter activity and 5'end sequences that contain two or three copies of TetO sites. The reverse universal primer is a long one that include three regions (a) a 3' end that target the 5' end of the promoter in a source polynucleotide, shRNA or siRNA or miRNA sequence, and a termination sequence. Once transfected in a cell line that expresses the repressor that is activated when doxycycline binds to, the shRNA is transcribed and inhibit the gene activity.

Figure 4:
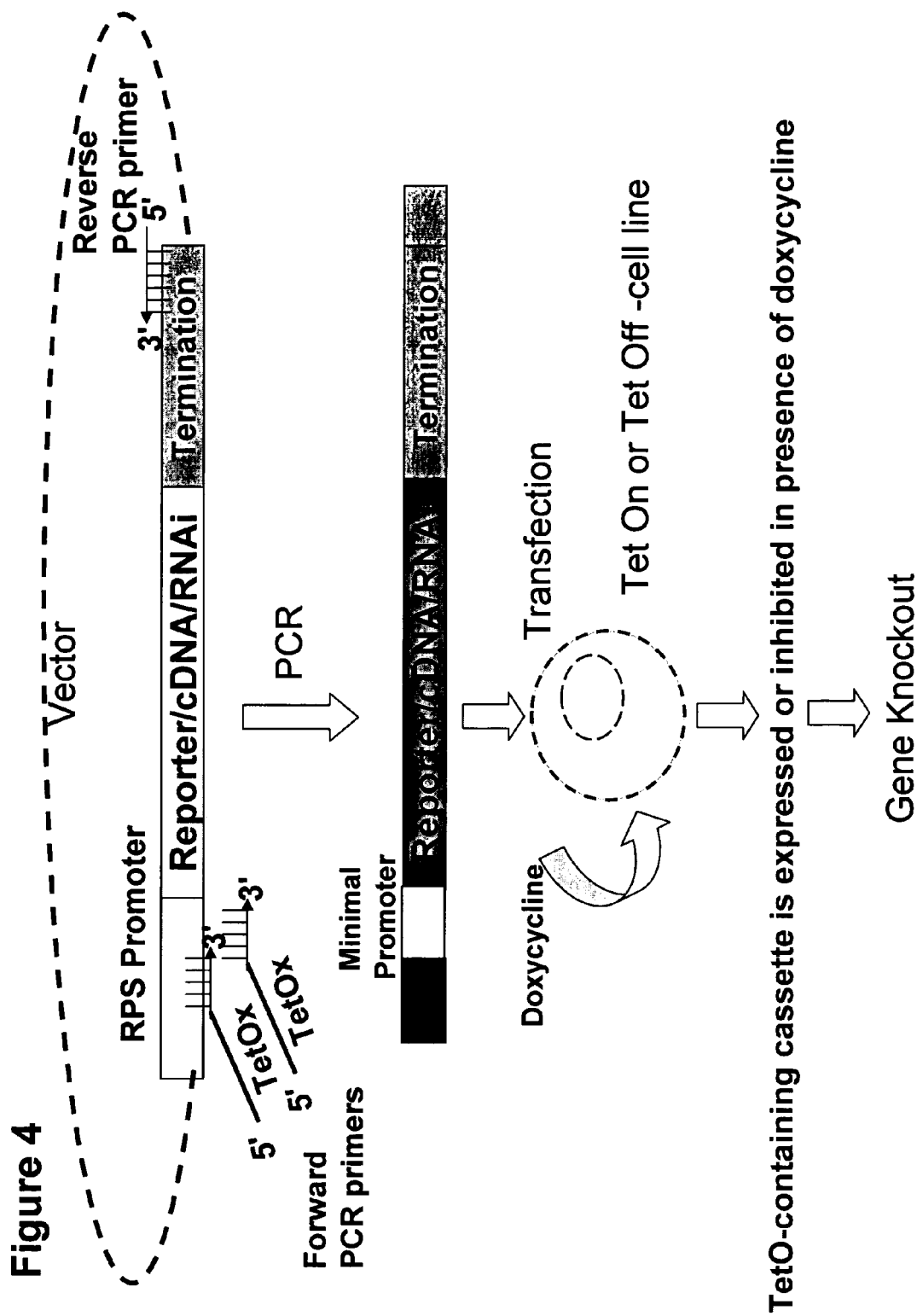

FIG. 4 Schematic representation for the strategy of constructing TetO-regulated expression linear cassette using cloning-free approach without plasmid or use of enzymes.

Linear constructs were generated by PCR that contains any where from one to more TetO copies, preferably two to three, since these are incorporated in the forward primer, and minimal ribosomal protein promoter arrangements.

FIG. 5

The forward primer (SEQ ID NOs. 27 and 28) incorporates different arrangements of the RPS30M1 promoter regions (−24 or −68 upstream from introduced TATA box in RPS30 promoter) along with three copies of TetO. The reverse primer is downstream of the polyA termination site. The PCR products were purified using Qiagen PCR cleanup column and 75 ng products were transfected into either HEK293 Tet-Off cell line. Doxycycline was added at 1.5 µg/ml to activate shut off transcription. After 48, the fluorescence of the HuR-GFP was quantitated.

The TetO$_3$-minimal promoter (−24) containing construct had better suppression in the presence of doxycycline (~87%) when compared to the construct with extended (−68) minimal promoter.

Figure 6:
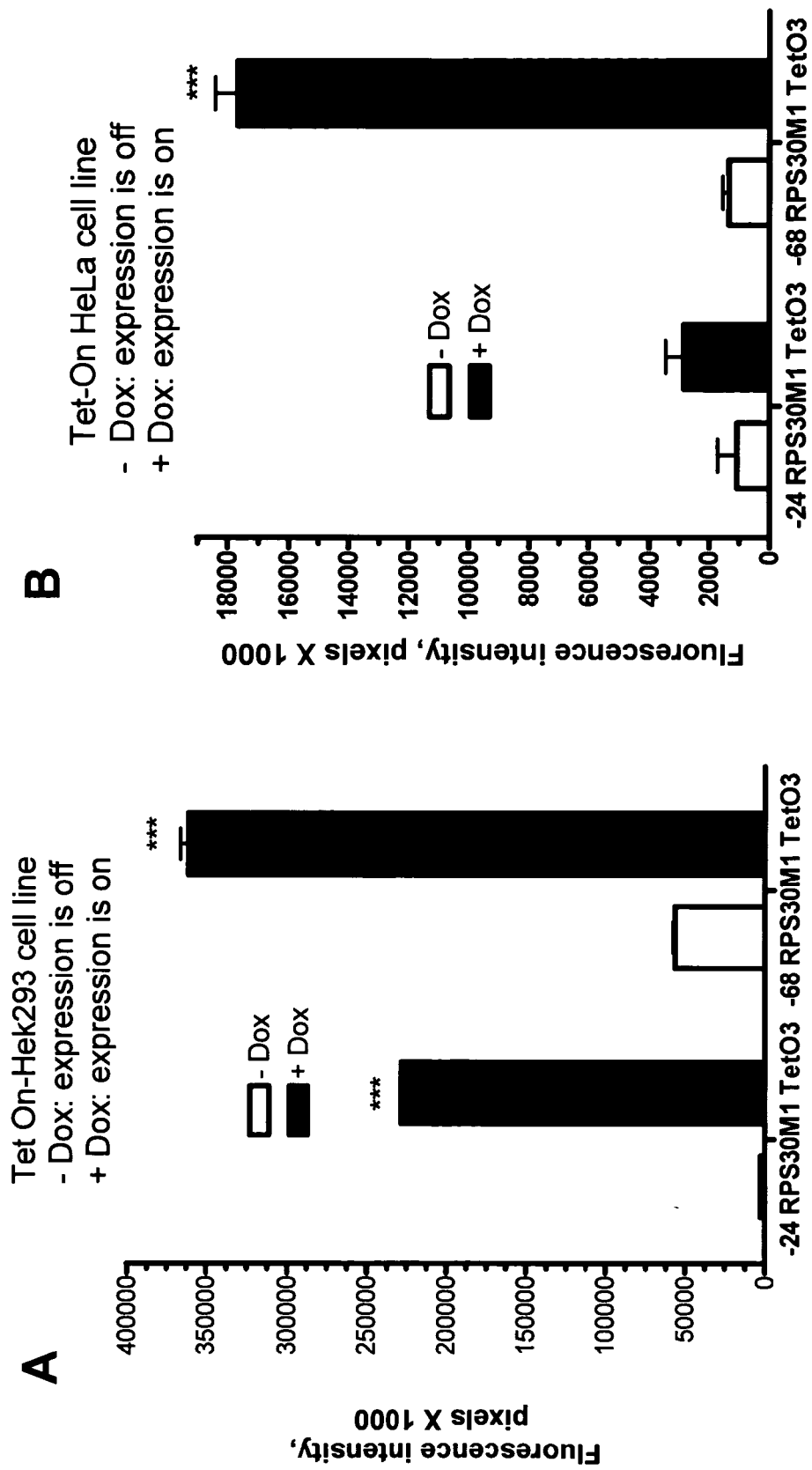

FIG. 6 Comparison between Tet-On Hek293 and Tet-Off Hela 293 cells.

We have used both Tet-On Hek293 (A) and Tet-Off Hela 293 (B). The −24 TetO3-linked PCR products were transfected into the cells. The −24 construct led to 77 fold induction of the linked gene in HEK293 with minimal leakage in absence of doxycycline whereas −68 construct led to more leakage and lower induction (6-fold). Whereas, in HeLa Tet-On the −24 construct did not lead to significant induction but with the −68 construct, 13 fold induction was achieved FIG. 7 Generation of expression-active linear PCR product from naked cDNA.

Schematic representation for the strategy of constructing TetO-regulated expression linear cassette using cloning-free approach without plasmid or use of enzymes and starting from just sequence that lacks expression competency (i.e., no promoter) such as cDNA or fragment. Linear constructs were generated by PCR that contains any where from one to more TetO copies, preferably two to three, since these are incorporated in the forward primer, and minimal promoter sequence are also incorporated in the forward primer. The forward primer has also 3'end region that targets any region upstream or at the initiation codon of the cDNA or gene fragment. The reverse primer is at downstream of the cDNA 3'UTR.

Figure 8:
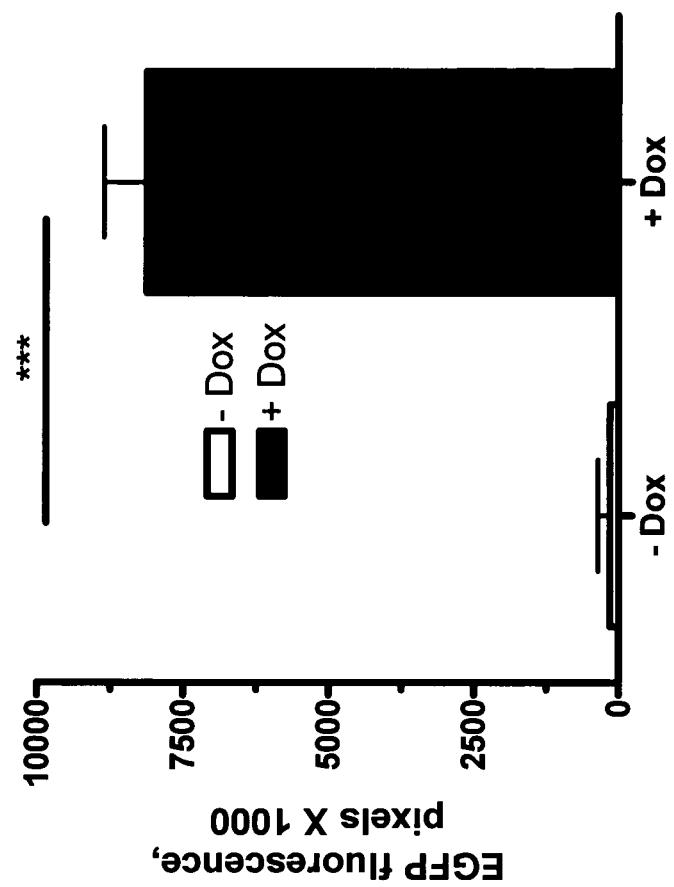

FIG. 8. A GFP cDNA that lacks a promoter and thus is not expressed was made expressed by amplification of the construct using a forward primers that has TATA box and other transcriptional control elements.

EXAMPLES

Example 1

Figure 1:
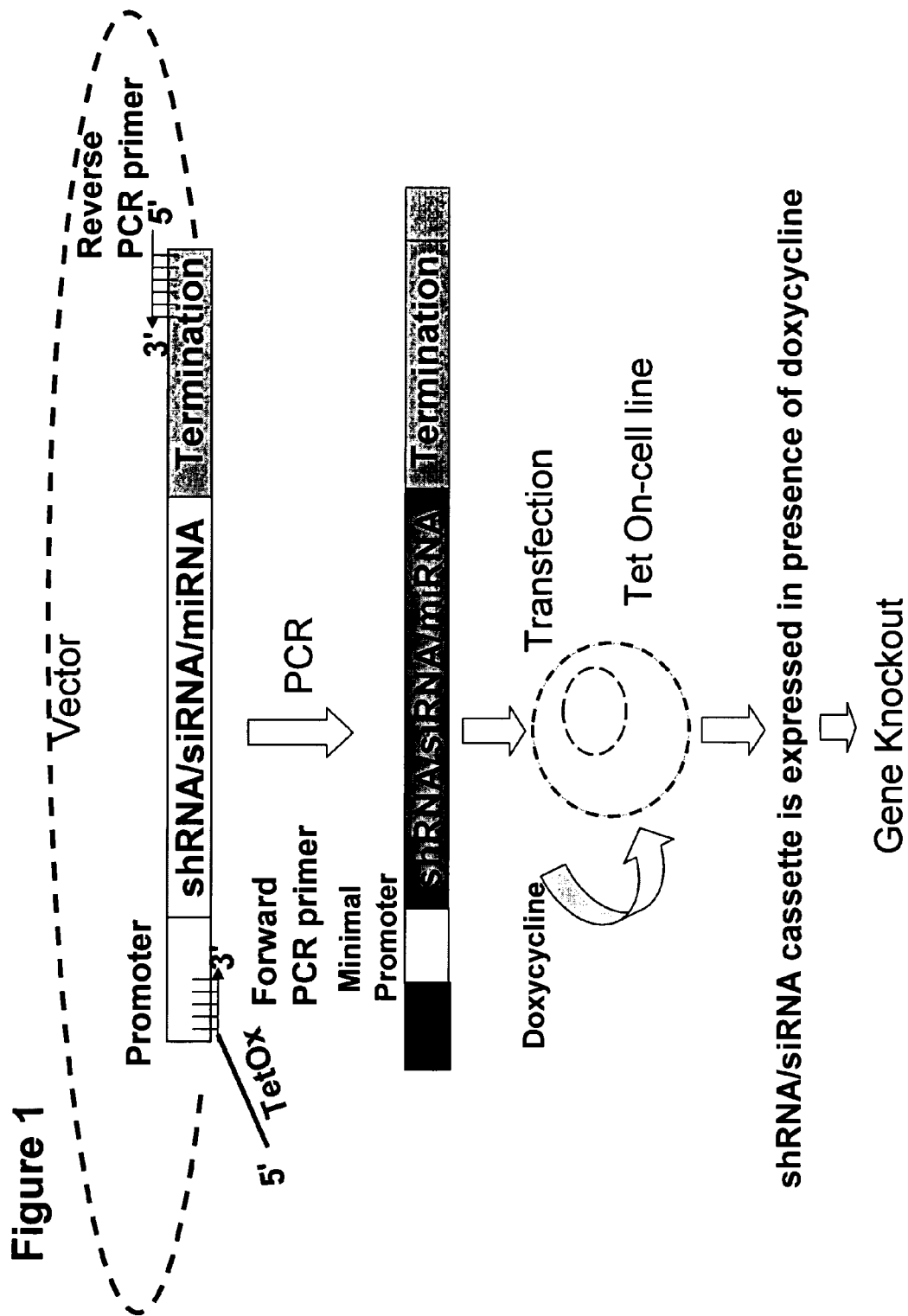
FIG. 1 Schematic representation of conversion of shRNA or any inhibitory RNA expressing vector, such as miRNA-based vector, into tetracycline-inducible gene without cloning ("top-down method").
Figure 2:
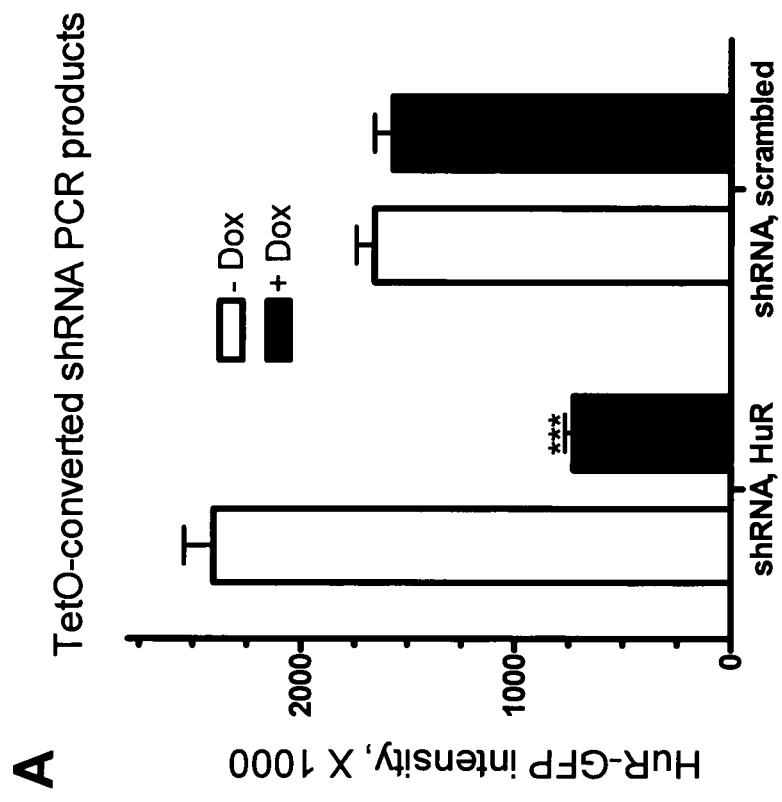

The short hairpin RNA (shRNA) vector against the RNA binding protein, HuR, was used as a source polynucleotide. This shRNA vector (Clone 4) is from SA biosciences (Maryland, U.S.) and it is under the control of U1 promoter. This shRNA vector was used as the source polynucleotide for amplifying the desired region (see FIG. 1). The forward primer (SEQ ID NOs. 15 to 17) incorporates different arrangements of the U1 minimal promoter region targeted along with three copies of TetO. The reverse primer is downstream of the termination site (SEQ ID NO. 18). The PCR product was purified using Qiagen PCR cleanup column and transfected into HEK293 cells that stably express the rtTA transactivator that is unable to bind TetO sequences and activate linked promoter transcription (Clontech, Inc, CA) along with HuR-GFP fusion expression vector. After 24 hours, the fluorescence of the HuR-GFP was quantitated (see FIG. 2). Similar to shRNA plasmids, the TetO-converted shRNA linear cassette was able to downregulate HuR-GFP protein levels when induced by doxycycline. Both knock down the gene activity by approximately 60% in approximately 20 hours and further knockdowns are expected with longer treatment, e.g., 70-90%.

Example 2

The forward primer (SEQ ID NOs. 27 and 28) incorporates different arrangements of the RPS30M1 promoter regions (−24 or −68 upstream from introduced TATA box in RPS30 promoter) along with three copies of TetO. The reverse primer is downstream of the polyA termination site. The PCR products were purified using Qiagen PCR cleanup column and 75 ng products were transfected into either HEK293 Tet-Off cell line. Doxycycline was added at 1.5 µg/ml to activate shut off transcription. After 48, the fluorescence of the HuR-GFP was quantitated.

Figure 5:
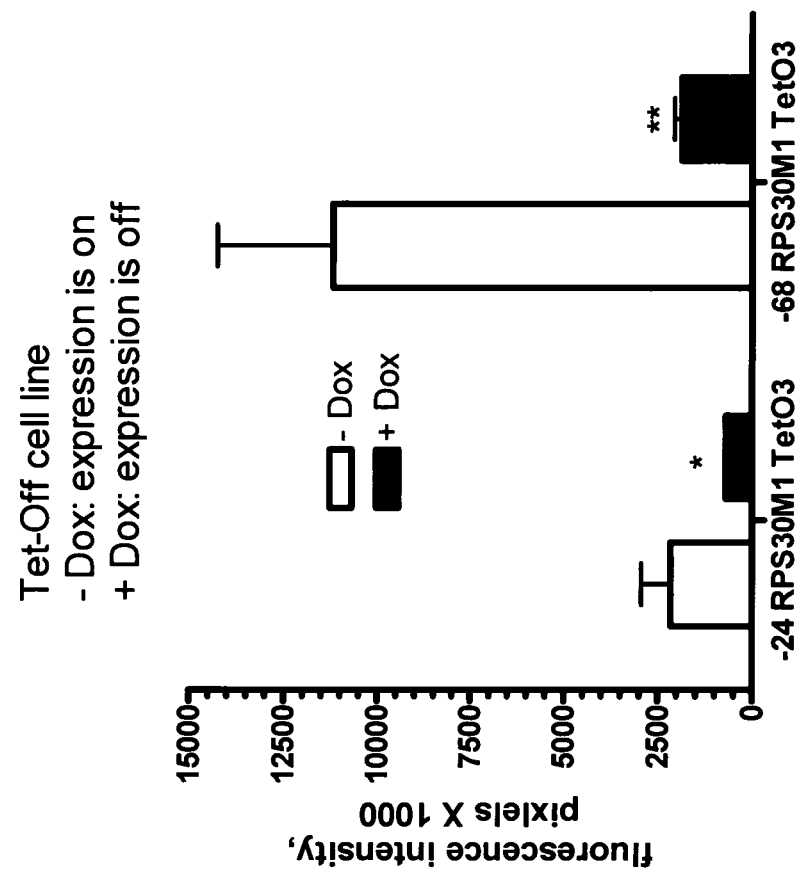

The TetO$_3$-minimal promoter (−24) containing construct had better suppression in the presence of doxycycline (~87%) when compared to the construct with extended (−68) minimal promoter (see FIG. 5). Doxycycline has no effect on EGFP linear control constructs that lack TetO sequences.

In Tet-On system, the cells stably express the rtTA transactivator that is unable to bind TetO sequences in absence of doxycycline, when doxycycline is added, it activates the TetO-linked promoter.

We have used both Tet-On Hek293 and Tet-Off Hela 293 (FIG. 6). The −24 TetO3-linked PCR products were transfected into the cells. The −24 construct led to 77 fold induction of the linked gene in HEK293 with minimal leakage in absence of doxycycline whereas −68 construct led to more leakage and lower induction (6-fold). Whereas, in HeLa Tet-On the −24 construct did not lead to significant induction but with the −68 construct, 13 fold induction was achieved (see FIG. 6).

Sequences of the Primers as Examples:

1. U1 Promoter System

```
Forward primer:
TetO3-40U1                               SEQ ID NO. 15
CATCCCTATCAGTGATAGACCATCCCTATCAGTGATAGACCATCCCTA
TCAGTGATGaggcgtatgaggctgtgt TetO3-80U1                               SEQ ID NO. 16
CATCCCTATCAGTGATAGACCATCCCTATCAGTGATAGACCATCCCTA
TCAGTGATAgtgcgcggggcaagtga TetO3-60U1                               SEQ ID NO. 17
CATCCCTATCAGTGATAGACCATCCCTATCAGTGATAGACCATCCCTA
TCAGTGATgtgaccgtgtgtgtaaagagt Reverse Primer:
U1 Termination                           SEQ ID NO. 18
CCAGTCTACTTTTGAAACTCC
```

2. U6 Promoter System

```
Forward:
TetO3-U6                                 SEQ ID NO. 19
CATCCCTATCAGTGATAGACCATCCCTATCAGTGATAGACCATCCCTA
TCAGTGATGGACTATCATATGCTTACCGT Reverse:
Promoter Primer                          SEQ ID NO. 20
ACGACGGCCAGTGCCAA
```

3. CMV Promoter:

```
TetO3-35                                 SEQ ID NO. 21
CATCCCTATCAGTGATAGACCATCCCTATCAGTGATAGACCATCCCTA
TCAGTG

TetO2-53                                 SEQ ID NO. 22
ACCAGGTCCCTATCAGTGATAGAGATCCTCCCTATCAGTGATAGAGAG
GTAGGCGTGTACGGTG

HuR shR-CMVE1                            SEQ ID NO. 23
GAAAAAAGAAGAGGCAATTACCAGTTTTGACAGGAAGAAACTGGTAAT
TGCCTCTTCTCGGTTCACTAAACGAGCT

HuR shR-U1                               SEQ ID NO. 24
GAAAAAAGAAGAGGCAATTACCAGTTTTGACAGGAAGAAACTGGTAAT
TGCCTCTTCTCGAGATCTTGGGCCTCTG

HuR shR-U6 (psilencer)                   SEQ ID NO. 25
AAAAGAAGAGGCAATTACCAGTTTTGACAGGAAGAAACTGGTAATTGC
CTCTTCTCGCGTCCTTTCCACAAG HuR shRsm-CMVE1                          SEQ ID NO. 26
AAGAAGAGGCAATTACCAGTTTCTCTTGAAAACTGGTAATTGCCTCTT
CCGGTTCACTAAACGAGCT
```

4. RPS30

```
TetO3-68TRPS30                           SEQ ID NO. 27
CATCCCTATCAGTGATAGACCATCCCTATCAGTGATAGACCATCCCTA
TCAGTGATAGACgctgcctgcccaggcaggttc TetO3-24T2RPS30                          SEQ ID NO. 28
CATCCCTATCAGTGATAGACCATCCCTATCAGTGATAGACCATCCCTA
TCAGTGATAGACggcggagctaggactgcctt
```

Examples 3

Figure 7:
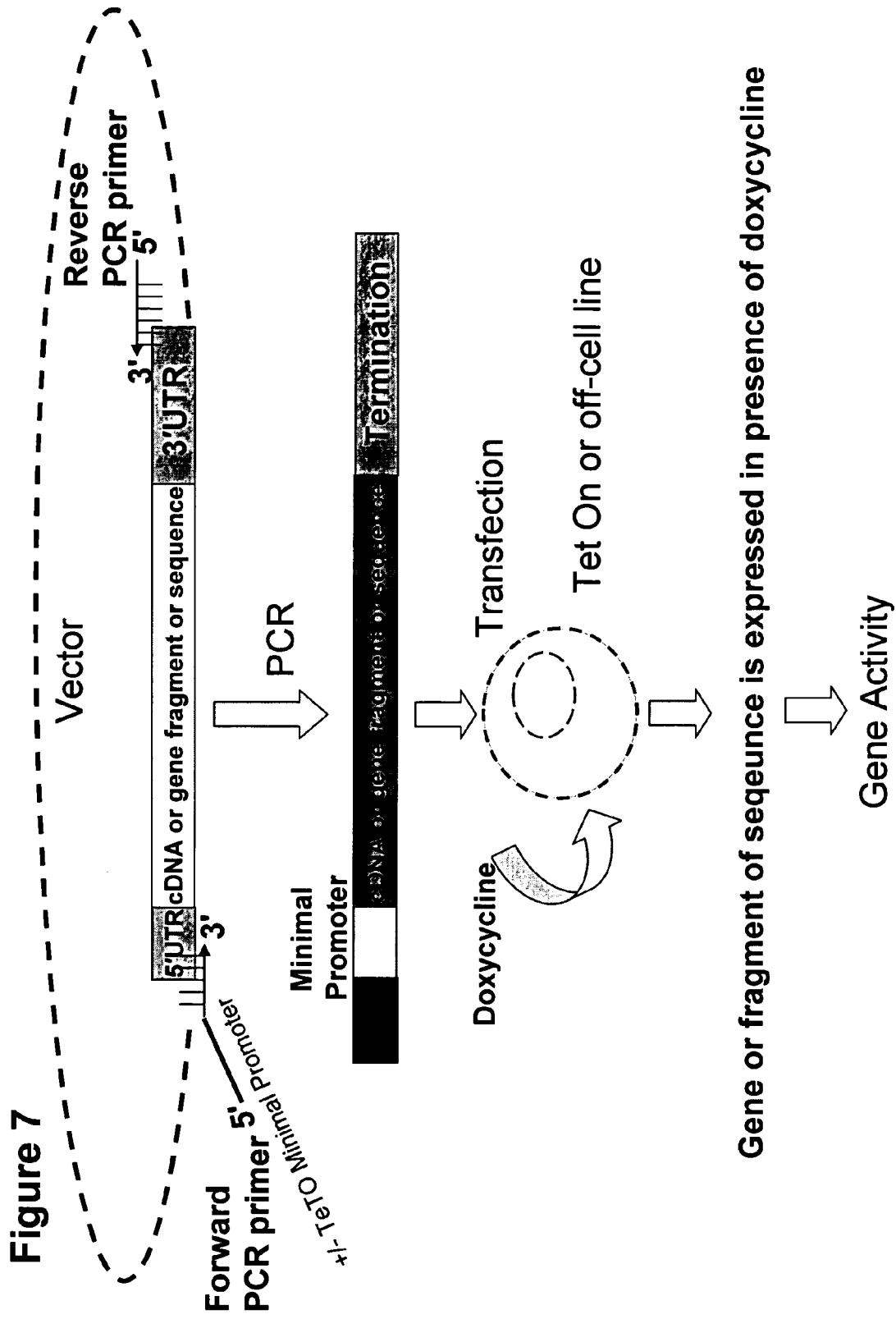

We have used naked cDNA that codes for GFP to convert it to expression ready cassette using PCR (FIGS. 7 and 8). The forward PCR primer (SEQ ID NO. 29) codes for TetO, minimal promoter, and sequence that are complementary at a region near the initiation codon of the cDNA. The reverse primer (SEQ ID NO. 30) targets a region downstream of the cDNA, i.e., downstream of the 3'UTR. When the PCR products are transfected onto cells, they express the cassette which now harbors a promoter. Any control sequence in the 5' end of the Forward primer can be used to enhance the expression.

```
                                         SEQ ID NO. 29
ACCAGGTCCCTATCAGTGATAGAGATCCTCCCTATCAGTGATAGAGAc tgggtatataatggaaGCCACCATGGCCAGCAAG
```

Underlined sequence: two copies of TetO2

Underlined italics: TATA box

Italics: directed at the initiation codon and includes Kozac

SEQ ID NO. 30
ACCAGGTCCCTATCAGTGATAGAGATCCTCCCTATCAGTGATAGAGAc tggg*tatataa*tggaa +vector targeting sequence upstream of the cDNA
Underlined sequence: two copies of TetO2
Underlined italics: TATA box
Italics: directed at the initiation codon and includes Kozac Ribosomal Protein Promoter Sequences and Preferred Modifications
1. RPS30

The starting sequence that the inventors used for their promoter modifications can be found on the RPG ribosomal protein gene database (http://ribosome.miyazaki-med.ac.jp/rpg.cgi?mode=strc&id=HUM10033).

See also SEQ ID NO. 1.

The gene of Homo sapiens RPS30 contains several intron and exon sequence sections as well as a 5' upstream and a 3' downstream region. The putative transcriptional initiation box is tacaaata (underlined).

5' Upstream
agcgtggccttgtttgtacctccatgattgcctggctggccttgctaa cctaatcacatctgtgacgggatatagtgatgtttaatcttatgattg ccttaagaattaaggcaatcagacgggttcggcggctcatgcctgtaa tcccagcactttgggaggccgaggcgggcggatcacgaggtcagaaga tccagtccatcctggctaacaaggtgaaacccgtctctactaaaaat acaaaaaattagccgggcatggtggcgggagcctgtagtcccagctac tcgggaggctgaggcaggaggatggcgtgaatctgggaggcggagctt gcagtgggccgagatcgcgccactgccctccagcctgggcgacagagc gagactccgtctcaaaaaaaaaaaaaaaaagaattaaggcaatcataa ttccccacgcacactcatatgctaggaccccgccccttacctgaaacg ttgtggcttatatagacactgccaggcactgtgttaagtgctcccaaa gagcacccagtctaccattttccctctcgattctatatgtacactcg ggacaagttctcctgatcgaaaacggcaaaactaaggcccccaagtagg aatgccttagttttcggggttaacaatgattaacactgagcctcacac ccacgcgatgccctcagctcctcgctcagcgctctcaccaacagccgt agcccgcagcccgctggacaccggttctccatcccgcagcgtagcc cggaacatggtagctgccatctttacctgctacgccagccttctgtgc gcgcaactgtctggtcccgccccgtcctgcgcgagctgcctgcccagg caggttcgccggtgcgagcgtaaaggggcggagctaggactgccttgg gcgg<u>tacaaata</u>gcagggaaccgcgcggtcgctcagcagtgacgtgac acgcagcccacggtctgtactgacgcgccctcgcttcttc Exon 1
CTCTTTCTCGACTCCATCTTCGCGGTAGCTGGGACCGCCGTTCAG Intron 1
gtaagaatgggccttggctggatccgaagggcttgtagcaggttggc tgcgggtcagaaggcgcgggggaaccgaagaacggggcctgctccg tggccctgctccagtccctatccgaactccttgggaggcctggccttc cccacgtgagccgccgcgaccaccatcccgtcgcgatcgtttctggac cgctttccactcccaaatctcctttatcccagagcatttcttggcttc tcttacaagccgtcttttctttactcag Exon 2
TCGCCAATATGCAGCTCTTTGTCCGCGCCCAGGAGCTACACACCTTCG

AGGTGACCGGCCAGGAAACGGTCGCCCAGATCAAG

Intron 2
gtaaggctgcttggtgcgccctgggttccattttcttgtgctcttcac tctcgcggcccgagggaacgcttacgagccttatctttccctgtag Exon 3
GCTCATGTAGCCTCACTGGAGGGCATTGCCCCGGAAGATCAAGTCGTG

CTCCTGGCAGGCGCGCCCTGGAGGATGAGGCCACTCTGGGCCAGTGC

GGGGTGGAGGCCCTGACTACCCTGGAAGTAGCAGGCCGCATGCTTGGAG

Intron 3
gtgagtgagagaggaatgttctttgaagtaccggtaagcgtctagtga gtgtggggtgcatagtcctgacagctgagtgtcacacctatggtaata gagtacttctcactgtcttcagttcagagtgattcttcctgtttacat ccctcatgttgaacacagacgtccatgggagactgagccagagtgtag ttgtatttcagtcacatcacgagatcctagtctggttatcagcttcca cactaaaattaggtcagaccagggcccccaaagtgctctataaaatta gaagctggaagatcctgaaatgaaacttaagatttcaaggtcaaatat ctgcaactttgttctcattacctattgggcgcagcttctctttaaagg cttgaattgagaaagaggggttctgctgggtggcaccttcttgctct tacctgctggtgccttcctttcccactacag Exon 4
GTAAAGTCCATGGTTCCCTGGCCCGTGCTGGAAAAGTGAGAGGTCAGA

CTCCTAAG

Intron 4
gtgagtgagagtattagtggtcatggtgttaggacttttttcctttc acagctaaaccaagtccctgggctcttactcggtttgccttctccctc cctggagatgagcctgagggaagggatgctaggtgtggaagacaggaa ccagggcctgattaaccttcccttctccag Exon 5
GTGGCCAAACAGGAGAAGAAGAAGAAGACAGGTCGGGCTAAGCGG

CGGATGCAGTACAACCGGCGCTTTGTCAACGTTGTGCCCACCTTTGGC

AAGAAGAAGGGCCCCAATGCCAACTCTTAAGTCTTTTGTAATTCTGGC

TTTCTCTAATAAAAAAGCCACTTAGTTCAGTC

3' Downstream
atcgcattgtttcatctttacttgcaaggcctcagggagaggtgtgct tctcggttggtggtatgtcccctaggagaacagtgaggcagaaaagg cagaagcctttggtatgggggaagaaatggtaaactacaagagaaat ttcctgtgaagaaacagctacagatcctgggggcttcagatgtaaaa ttggggttattccctatcctaagtaacttgatcagtcccccaggtca ttcttttcatcttctaaacagagaaggtagcaggaatcactgtggtg agaggtttgttatggaggcagcaatagaaagggatgggtggggaagag -continued

```
gtttgtatagaaggtgaacctggccgttccctgaacttggtaccagct gtggccttagagtccagggcaggaatctggtctgccttggttttagaa gtaaatattatgttgggagcatggcctcgtttgtacctctgtgactgc ctggccggacttggtaacctaatcacatctgtgattggatatagtgag gtttcagtgttcccaaaagttgggttacctctggggctgattcagggt tctcttctggcaactgagcctcccagcacttctgaaccccacttactc attcagctaaagtttctggacctgccagttcttgagaaatagcatcca acagggtaaagcccttgggctgtggactttgactgcctgagtttggac cttcttttcttcctactccatttactgggtggctggcctttgaacta actactaatttaatctctgccatctccagggctgctgtgagggttaaa ggatgtaaatcaacatctggcttacagtgagtgtgtgaatcttggcta tttttgtctctgtggtgttaaagacatggtttctgccttccagcagtt tagaaaggggaggatgtggacagatacaatagcatcccagagagggc ctctttttttgttttcttttttctttattttattttatt
```

2. RPS23

The starting sequence that the inventors used for their promoter modifications can be found on the RPG ribosomal protein gene database (http://ribosome.miyazaki-med.ac.jp/rpg.cgi?mode=strc&id=HUM10025).

See also SEQ ID NO. 2.

The gene of Homo sapiens RPS23 contains several intron and exon sequence sections as well as a 5' upstream and a 3' downstream region.

```
5' Upstream
gtctggcacatagaaggcattttaaacatccttgctgagtgaaccaa tatcccagaaacctctcacagctagttcatcttacaggagaaacagta ttaaagagttaattaaatggccaggcgcggtggctcacgcctgtaatc ccagcacattgggaggccgaggcgggcggatcactcgaggtcaggaga tcgacaccagcctggccaacatggtgaaaccccctctctactgaaaat acaaacatcagccaggcgtgatggtggaagcctgtaatcccagctact caggaggctgaggtgggacaatcgcttgaacccgggaggcggaggttg tagtgagccaagatcgcaccactgcacaacagcctagaagacagagtg agaccctgtctcagaaaaaataaaaataaaaataaatctataa gtaaatgactcgccagtcaaaataaacggcaactttaggqttaaaqqc ccaatctggctccaaagcttgggqttttagttactacactacattgct tcactatattttacaatttactagctgcttataaqtatgaattaaqqc tcagaagtctaattttccagactactcggaggactctcgccccactcc actccacaaagattcagctcagcgactccttcctactctgacctagcc ccgcgtcccgctctcagtggcttgggcaagagcgcctgcgcggtgagc gggtcccataaaacgcattctgggattggtagtccatgttcctccggt ctccagcattcaaaagaaaaggggaaaaaaaaccatgcaaattaga tatctctgaatttcttgcaaattaaataagacgcagattctggctcag gaaagtgatgcaaacgcgtcgttttcaaaggagagaccccagcctcgg
```

```
gtcaggcgcggcgcagacagcggcgcggggtccttggctgggcgggc ttgctcgcggtggcttgtggctccttcctgcggtgcttct
```

```
Exon 1
CTCTTTCGCTCAGGCCCGTGGCGCCGACAGGATGG
```

```
Intron 1
gtgagctgttgtggccggtttaagggcgctgcaagcgggacttggggt cttggggacgggcgggcggatgcgaatagagtagggcggggatgcca tggagaggctccatggggagggccggggaagcgccgctccaggaggc acgtggtccggcgcggaaggggcccatgaggcgtggaggccgccgagg tcggggtaccgagggacgcagggaggccagcgcttcctcccgggcatt cgagcgggcctcgtccttcgggagaacacattctccggagccctctt cgaacgtttattagtcggttcagggcaacttgaaggccaaatgtttgg cccacaggccaataaatagtacgagagccaatcggcttaagggtttat tccaggtgaggcgagtgtcttagaagatgggaaacacgtagatggcgt gttttacggaagaactaaaatatttaattttag
```

```
Exon 2
GCAAGTGTCGTGGACTTCGTACTGCTAGGAAGCTCCGTAGTCACCGAC

GAGACCAGAAGTGGCATGATAAACAGTATAAGAAAGCTCATTTGGGCA

CAGCCCTAAAGGCCAACCCTTTTGGAGGTGCTTCTCATGCAAAAGGAA

TCGTGCTGGAAAAAGT
```

```
Intron 2
gtaagtccattgctcccgtcaagttttagtttattataggaattcgag acatgaacttacgaattcttgttttgaaagtaattgcaggttttgtg tagtagtattcatttgggcattgtggggtaaaattgcaaagcgtttgt tctatttaaaagttggtaaaattagttttttgggaattaggtagttaag gttttaatttaacgttggcctggaaggaattggagaagatactagcaa tgatgaagtaaaggacacaaacacctttactgtgggagttgttataag taaatggcacgtgtcagctattgaactttatcgacttgataaaactaa ggtgaagagaagtgacttgcatcagaattaattgaggtcatacaccta agattgagacatgaaactgccagtatttgactggttttgactttttaa aataataatttcatatagttctatcatatttgatggtagagccatttt aacccagacttttttttttttttttttttttgagacagtctagct ctgtcacccaggctggtgtgcagtagcgcaagactccctgcaacctta gcctcccaggttcaagcatttctcctgcctcagcctcccaggtagctg ggattacaggcgcccactaccacaccagctaatattttgtattttcag tagtgatggggtttcaccatgttgaccaggctagtctcaaactcctga cctcaggtgataatgcctgcttcggcctccgaaagtgctggaattaca ggcgtgagccactgtgtccggcccagactttctaattcttacctcaga tacctttttctttttcttttttttttttgagatagggtcccttgt cacacaggctggccatcttgacgttctaggcatagatcctcccacgtc agcctcgcaagtagttgggactacaggcccacgctgccactccagtct actttttataactgtaaaaggtctagaaatttcccccattgtgctaatg
```

-continued
aaattaagactggcagaaaactaggttgacatcacaggacttcagctc agccatttgaggttagattgaaaagatagaaacagtttctcattagtt ctctagttaatatgaaaagataatcttttcagaaagccagctcacag tgctgtgccttttgtatttcag Exon 3
AGGAGTTGAAGCCAAACAGCCAAATTCTGCCATTAGGAAGTGTGTAAG

GGTCCAGCTGATCAAGAATGGCAAGAAAATCACAGCCTTTGTACCCAA

TGACGGTTGCTTGAACTTTATTGAG

Intron 3
gtgagtatttcaactctatcgtaccttctgttcttggggtggcctccc tcacattttatctgatgcaagggagtttcctcacatgaaagtatttt tgtgatcgccaccaacaccagaaataaacttcttatttattccag Exon 4
GAAAATGATGAAGTTCTGGTTGCTGGATTTGGTCGCAAAGGTCATGCT

GTTGGTGATATTCCTGGAGTCCGCTTTAAGGTTGTCAAAGTAGCCAAT

GTTTCTCTTTTGGCCCTATACAAAGGCAAGAAGGAAAGACCAAGATCA

TAAATATTAATGGTGAAAACACTGTAGTAATAAATTTTCATATGCC

3' Downstream
aaaaaatgtttgtatcttactgtccctgttctcaccacgaagatcat gttcattaccaccaccaccccccccttatttttttatcctaaaccagc aaacgcaggacctgtaccaattttaggagacaataagacagggttgtt tcaggattctctagagttaataacatttgtaacctggcacagtttccc tcatcctgtggaataagaaaatgggatagatctggaataaatgtgcag tattgtagtattacttaagaacttcaagggaacttcaaaaactcact gaaattctagtgagatactttcttttttattcttggtattttccatat cgggtgcaacacttcagttaccaaatttcattgcacatagattatctt aggtaccttggaaatgcacattcttgtatccatcttacaggggccca agatgataaatagtaaactcaaaattgctccccactctgtttattatt taaaggtgtcaggatctgtgttgtaatgtgtctacattaatgtgttta ggagaatacaggcattggatcatttagttgatggaagtatatgccagg caagggagataaggtatacgacaagactgatgttttcagtatcttctc atgaggttgtcagagaccttcatgtcttcaaagactagtcagcaaatg aagtggtttagtgtagagacaagattggttgtgttttgataatttaag ctaggtattgagtacatgtggattttgctgtccacaaatacttgttc agagttttcatggatacagtggcatggttgaaatgaagctgtgagcct tctgctttaaatctgatgtaagaaactcctgttaacaaatagtaagta tgggttaattagcccttgatcaaagcctagctttacattgtttagga tctttggaaaacaattggtttggttgcccactttccgtaggatcaaga gcagaacctttcacatggcacagaagaacccaggttgcgc

3. RPS30I-M1

SEQ ID NO. 3
Gatatcggcaaaactaaggccccaagtaggaatgccttagttttcggg gttaacaatgattaacactcctgagcctcacacccacgcgatgccctc agctcctcgctcagcgctctcaccaacagccgtagcccgcagcccgc tggacaccgggtctccatccccgcagcgtagcccggaacatggtagct gccatctttacctgctacgccagccttctgtgcgcgcaactgtctgg*t*

*cccgccccgtcctgcg*cgagctgcctgcccaggcaggttcgccggtgc gagcgtaaa*ggggcggagc*taggactgccttgggcggtataaatagca gggaaccgcgcggtcgctcagcagtgacgtgacacgcagcccacggtc tgtactgacgcgccctcgcttcttcctctttctcgactccatcttcgc ggtagctgggaccgccgttcaggtaagaatggggccttggctgcagcc gaagggcttgtagcaggttggctgcggggtcagaaggcgcgggggaa ccgaagaacggggcctgctccgtggccctgctccagtccctatccgaa ctccttgggaggcctggccttccccacgtgagccgccgcgaccaccat cccgtcgcgatcgtttctggaccgctttccactcccaaatctccttta tcccagagcatttcttggcttctcttacaagccgtcttttctttactc agtcgccg*tcgac*

Modifications
1. 5' truncated RPS30 promoter (+from transcriptional start site),
2. 60 bases were added that include sp1 site,
3. RPS30 exon 1,
4. first intron of RPS30, and
5. nine bases of exon 2 RPS23 for splicing.
6. The putative transcriptional initiation box was improved from tacaaata to tataaata.
7. BamH1 site CA$\overline{CTGAG}$ was eliminated by mutating to CA$\overline{CCTTGAG}$.

RPS30-M1 (SEQ ID NO. 3) is a 5'-truncated promoter in which 600 bases were deleted from the 5'end of the wild type promoter sequence (SEQ ID NO. 1). RPS30-M1 has two sp1 sites: TCCCGCCCCGTCCTGCG (position 230-250) and GGGGCGGAGC (position 290-300).

4. RPS30I-M2

SEQ ID NO. 4
Gatatcta*gccgggcatggtggcggg*agcctgtagtcccagctactcg ggaggctgaggcaggaggatggcgtgaatct*gggaggcggagc*ttgca gtgggccgagatcgcgccacttgagcctcacacccacgcgatgccctc agctcctcgctcagcgctctcaccaacagccgtagcccgcagcccgc tggacaccgggtctccatccccgcagcgtagcccggaacatggtagct gccatctttacctgctacgccagccttctgtgcgcgcaactgtctgg*t*

*cccgccccgtcctgcgcg*agctgcctgcccaggcaggttcgccggtgc gagcgtaaa*ggggcggagc*taggactgccttgggcggtacaaatagca gggaaccgcgcggtcgctcagcagtgacgtgacacgcagcccacggtc tgtactgacgcgccctcgcttcttcctctttctcgactccatcttcgc ggtagctgggaccgccgttcaggtaagaatggggccttggctgcagcc gaagggcttgtagcaggttggctgcggggtcagaaggcgcgggggaa ccgaagaacggggcctgctccgtggccctgctccagtccctatccgaa ctccttgggaggcctggccttccccacgtgagccgccgcgaccaccat -continued cccgtcgcgatcgtttctggaccgctttccactcccaaatctccttta tcccagagcatttcttggcttctcttacaagccgtcttttctttactc agtcgccgtcgac Modifications
1. 5' truncated RPS30 promoter (+from transcriptional start site),
2. 100 bases were added that include sp1 site,
3. RPS30 exon 1,
4. first intron of RPS30, and
5. nine bases of exon 2 RPS23 for splicing.
6. /
7. BamH1 site CACTGAG was eliminated by mutating to CACCTTGAG RPS30-M2 (SEQ ID NO. 4) is a 5'-truncated promoter in which 535 bases were removed from the wild type sequence of SEQ ID NO1. A 100 bases (position of wild type) that contain additional sp1 site was added: (position of 4-21 GCCGGGCA TGGTGGCGGG) and (position 75-87 GGGAGGC GGAGC). In addition to the following sp1 sites: TCCCGCCCCGTCCTGCG (position: 281-297) and GGGGCGGAGC (position 340-49). Thus, RPS30-M2 contains 4 sp1 sites.
5. RPS30I-M2T SEQ ID NO. 5
Gatatcta*gccgggcatggtggcggg*agcctgtagtcccagctactcg ggaggctgaggcaggaggatggcgtgaatct*gggaggcggagc*ttgca gtgggccgagatcgcgccacttgagcctcacacccacgcgatgccctc agctcctcgctcagcgctctcaccaacagccgtagcccgcagcccgc tggacaccgggtctccatcccgcagcgtagcccggaacatggtagct gccatctttacctgctacgccagccttctgtgcgcgcaactgtctgg*t*

*ccgccccgtcctgcg*cgagctgcctgcccaggcaggttcgccggtgc gagcgtaaa*ggggcggagc*taggactgccttgggcggtataaatagca gggaaccgcgcggtcgctcagcagtgacgtgacacgcagcccacggtc tgtactgacgcgccctcgcttcttcctctttctcgactccatcttcgc ggtagctgggaccgccgttcaggtaagaatggggccttggctgcagcc gaagggcttgtagcaggttggctgcggggtcagaaggcgcgggggaa ccgaagaacggggcctgctccgtggccctgctccagtccctatccgaa ctccttgggaggcctggccttccccacgtgagccgccgcgaccaccat cccgtcgcgatcgtttctggaccgctttccactcccaaatctccttta tcccagagcatttcttggcttctcttacaagccgtcttttctttactc agtcgccgtcgac Modifications
1. 5' truncated RPS30 promoter (+from transcriptional start site),
2. 100 bases were added that include sp1 site,
3. RPS30 exon 1,
4. first intron of RPS30, and
5. nine bases of exon 2 RPS23 for splicing.
6. The putative transcriptional initiation box was improved from tacaaata to tataaata.
7. BamH1 site CACTGAG was eliminated by mutating to CACCTTGAG.

A 100 bases (position of wild type) that contain additional sp1 site was added: GCCGGGCA TGGTGGCGGG and GGGAGGC GGAGC. In addition to the following sp1 sites: TCCCGCCCCGTCCTGCG and GGGGCGGAGC. Thus, RPS30-M2T contains 4 sp1 sites.
6. RPS23I-M SEQ ID NO. 6
Gatatctggccaggcgcggtggctcacgcctgtaatcccagcacattg ggaggccgaggcgggcggatcactcccagactactcggaggactctcg ccccactccactccacaaagattcagctcagcgactccttcctactct gacctagcccgcgtcccgctctcagtggcttgggcaagagcgcctgc gcggtgagcgggtcccataaaacgcattctgggattggtagtccatgt tcctccggtctccagcattcaaaagaaaaggggggaaaaaaaaccatg caaattagaatctctgaatttcttgcaaattaaataagacgcagattc tggctcaggaaagtgatgcaaacgcgtcgttttcaaaggagagacccc agcctcgggtcaggcgcggcgcagacagcggcgcgggtccttggctg ggcggggcttgctcgcggtggcttgtggctccttcctgcggtgcttct ctctttcgctcaggcccgtggcgccgacaggctgggtgagctgttgtg gccggtttaagggcgctgcaagcgggacttggggtcttggggacgggc gggcggatgcgaatagagtagggcgggggatgccatggagaggctcca tggggagggccggggaagcgccgctccaggaggcacgtggtccggcg cggaagggcccatgaggcgtggaggccgccgaggtcggggtaccgag ggacgcagggaggccagcgcttcctcccgggcattcgagcggggcctc gtccttcgggagaacacattctccggagccctcttcgaacgtttatta gtcggttcagggcaacttgaaggccaaatgtttggcccacaggccaat aaatagtacgagagccaatcggctaagggtttattccaggtgaggcga gtgtcttagaagatgggaaacacgtagatggcgtgttttttacggaaga actaaaatatttaattttttagGCAAGgtcgac Modifications
1. 5' truncated promoter (+392 from transcriptional start site),
2. addition of 68 bases of Sp1 site-containing sequences of RPS23 (+806 to +872 from transcription start site),
3. RPS23 exon 1,
4. first intron of RPS23, and
5. nine bases of exon 2 RPS23 for splicing.
6. /
7. The ATG site in exon 1 was mutated to CTG.
7. RPS30I-M1TOD SEQ ID NO. 7
Gatatcggcaaaactaaggccccaagtaggaatgccttagttttcggg gttaacaatgattaacactcctgagcctcacacccacgcgatgccctc agctcctcgctcagcgctctcaccaacagccgtagcccgcagcccgc tggacaccgggtctccatcccgcagcgtagcccggaacatggtagct gccatctttacctgctacgccagccttctgtgcgcgcaactgtctgg*t*

*ccgccccgtcctgcg*cgagctgcctgcccaggcaggttcgccggtgc gagcgtaaa*ggggcggagc*taggactgccttgggcggtataaatagca -continued gggaCATCCCTATCAGTGATAGACCATCCCTATCAGTGATAGACCATC

CCTATCAGTGATAGACaccgcgcggtcgctcagcagtgacgtgacacg cagcccacggtctgtactgacgcgccctcgcttcttcctctttctcga ctccatcttcgcggtagctgggaccgccgttcaggtaagaatggggcc ttggctgcagccgaagggcttgtagcaggttggctgcggggtcagaag gcgcgggggaaccgaagaacggggcctgctccgtggccctgctccag tccctatccgaactccttgggaggcctggccttccccacgtgagccgc cgcgaccaccatcccgtcgcgatcgtttctggaccgctttccactccc aaatctcctttatcccagagcatttcttggcttctcttacaagccgtc ttttctttactcagtcgcc*gtcgac*

Modifications

Same as RPS30I-M1 (SEQ ID NO. 3), namely
1. 5' truncated RPS30 promoter (+from transcriptional start site),
2. 60 bases were added that include sp1 site,
3. RPS30 exon 1,
4. first intron of RPS30, and
5. nine bases of exon 2 RPS23 for splicing.
6. The putative transcriptional initiation box was improved from tacaaata to tataaata.
7. BamH1 site CA$\overline{\text{CTGAG}}$ was eliminated by mutating to CACCTTGAG.
in addition
8. includes tetO sequences (bold) for regulatable of transcription downstream of the TATAAA (underlined) signal.
RPS30-M1 has two sp1 sites: TCCCGCCCCGTCCTGCG and GGGGCGGAGC.
8. RPS30I-M1TOU

SEQ ID NO. 8

Gatatcggcaaaactaaggccccaagtaggaatgccttagttttcggg gttaacaatgattaacactcctgagcctcacacccacgcgatgccctc -continued agctcctcgctcagcgctctcaccaacagccgtagcccgcagcccgc tggacaccgggtctccatccccgcagcgtagcccggaacatggtagct gccatctttacctgctacgccagccttctgtgcgcgcaactgtctgg*t*

*cccgccccgtcctgcg*cgagctgcctgcccaggcaggttcgccggtgc gagcgtaaaggggCATCCCTATCAGTGATAGACCATCCCTATCAGTGA TAGACCATCCCTATCAGTGATAGACcggagctaggactgccttgggcg g<u>tataaata</u>gcagggaaccgcgcggtcgctcagcagtgacgtgacacg cagcccacggtctgtactgacgcgccctcgcttcttcctctttctcga ctccatcttcgcggtagctgggaccgccgttcaggtaagaatggggcc ttggctgcagccgaagggcttgtagcaggttggctgcggggtcagaag gcgcgggggaaccgaagaacggggcctgctccgtggccctgctccag tccctatccgaactccttgggaggcctggccttccccacgtgagccgc cgcgaccaccatcccgtcgcgatcgtttctggaccgctttccactccc aaatctcctttatcccagagcatttcttggcttctcttacaagccgtc ttttctttactcagtcgcc*gtcgac*

Modifications

Same as RPS30I-M1 (SEQ ID NO. 3), namely
1. 5' truncated RPS30 promoter (+from transcriptional start site),
2. 60 bases were added that include sp1 site,
3. RPS30 exon 1,
4. first intron of RPS30, and
5. nine bases of exon 2 RPS23 for splicing.
6. The putative transcriptional initiation box was improved from tacaaata to tataaata.
7. BamH1 site CA$\overline{\text{CTGAG}}$ was eliminated by mutating to CACCTTGAG.
in addition
8. includes tetO sequences (bold) for regulatable of transcription upstream of the TATAAA (underlined) signal.

The invention claimed is:

1. A method for producing inducible expression active linear gene constructs, comprising the step of:
   (a) generating an inducible expression active linear gene construct, comprising
      one or more control element(s) that are inducible element(s),
      a minimal promoter comprising a transcriptionally non-inducible constitutively active ribosomal protein gene promoter,
      a DNA sequence selected from a gene, a coding region, an open reading frame (ORF), an inhibitory RNA coding sequence and a cDNA,
      a 3' untranslated region (3' UTR) containing mRNA destabilization or stabilization elements of a 3' UTR of a cellular mRNA, and
      a termination sequence,
   wherein the generating step comprises a PCR amplification of a source expression polynucleotide comprising in 5' to 3' direction a promoter sequence and the DNA sequence using
      (i) a forward primer comprising
         at its 3' end, a first sequence part complementary to a promoter region of the source expression polynucleotide upstream of the DNA sequence, and
         at its 5' end a second sequence part comprising one or more introduced control element(s); and
      (ii) a reverse primer selected from
         a reverse primer complementary to a region of the source expression polynucleotide downstream of the DNA sequence, wherein the primer comprises mRNA destabilization or stabilization elements of a 3' UTR of a cellular mRNA and a termination sequence, or
         a reverse primer complementary to a region of the source expression polynucleotide downstream of a 3' UTR wherein the region contains mRNA destabilization or stabilization elements of a 3' UTR of a cellular mRNA,
   wherein the source expression polynucleotide is a vector, a lentivirus, a plasmid, a virus-based vector, or a linear or linearized or amplified fragment thereof,
   wherein the mRNA destabilization elements are selected from AU-rich elements, GU-rich elements, and U-rich sequences,
   wherein the mRNA stabilization elements are selected from GC-rich elements, CU-rich elements, and UG-rich sequences,
   wherein the generating step does not involve a cloning step, wherein said cloning step includes the use of one or more of restriction digestion, cloning enzyme(s), bacterial transformation and plasmid preparation, and
   wherein expression of the inducible expression active linear gene construct resulting from (a) can be induced by the addition of a compound that activates the expression or by the withdrawal of a compound that represses the expression.

2. The method of claim 1, further comprising the following steps:
   (b) transfecting a cell or cell line with the inducible expression active linear gene construct obtained in step (a) of claim 1; wherein the cell or cell line transiently or stably expresses a repressor system,
   (c) expressing a protein encoded by the DNA sequence contained in the inducible expression active linear gene construct obtained in step (a) of claim 1 by the addition of a compound that activates the expression or by the withdrawal of a compound that represses the expression; and
   (d) measuring gene expression level or activity of the protein expressed in step (c).

3. The method according to claim 1, wherein the minimal promoter is a RPS23 promoter or a RPS30 promoter, which is modified for higher expression by modifying the transcriptional initiation sequence.

4. The method according to claim 3, wherein the minimal promoter further comprises at least one sp1 site-containing sequence.

5. The method according to claim 3, wherein the minimal promoter further comprises
   intron sequence(s) of ribosomal proteins,
   exon sequence(s) of ribosomal proteins, and/or
   modified sequences wherein the modification eliminates a restriction site.

6. The method according to claim 3, wherein the minimal promoter comprises a nucleic acid sequence of any of SEQ ID NOs. 3 to 8.

7. The method according to claim 1, wherein the termination sequence comprises an eukaroytic polyadenylation signal, pol III termination signal, thymidines stretch, U1 termination signal, pol I termination signal, or a synthetic termination variant.

8. The method according to claim 1, wherein the inducible control element is selected from the group consisting of a tetracycline (TetO) system, an ecdysone inducible system, a heat shock on system, a lacO/IPTG system, a cre system, a cumate repressor protein CymR system, a nitroreductase system, a coumermycin/novobiocin-regulated system, a RheoSwitch Ligand RSL 1 system, a chimeric bipartite nuclear receptor expression system, a GAL4 system.

9. The method according to claim 1, wherein the inducible control elements are CpG island containing sequences.

10. The method according to claim 1, wherein the forward primer comprises one or more regulatory sequence element(s) or transcriptional element(s) selected from transcriptional enhancing and translational enhancing element(s).

11. The method according to claim 1, wherein the forward primer comprises a nucleic acid sequence selected from SEQ ID NOs. 13 or 14.

12. The method according to claim 1, wherein the DNA sequence encodes a gene which is selected from the group consisting of: reporters, fluorescent reporters, green fluorescent protein (GFP) and derivatives, enhanced green fluorescent protein (EGFP) and derivatives, luciferase, modified luciferase, inhibitory RNA coding sequences, secreted reporter forms, alkaline phosphatase, CAT, β-galactosidase, antibodies, immunoglobin fragments, cDNA fragments, open reading frames (ORF), and domain sequences.

13. The method according to claim 1, wherein the inhibitory RNA coding sequence is selected from a coding DNA sequence for short hairpin RNA (shRNA), small interfering RNA (siRNA), micro RNA (miRNA) and antisense RNA.

14. A method for producing repressible expression active linear gene constructs, comprising the step of:
   (a) generating a repressible expression active linear gene construct, comprising
      one or more control element(s) that are inducible element(s),
      a minimal promoter comprising a transcriptionally non-inducible constitutively active ribosomal protein gene promoter, a DNA sequence selected from a gene, a coding region, an open reading frame (ORF) an inhibitory RNA coding sequence and a cDNA,
a 3' untranslated region (3' UTR) containing mRNA destabilization or stabilization elements of a 3' UTR of a cellular mRNA, and
a termination sequence,
wherein the generating step comprises a PCR amplification of a source expression polynucleotide comprising in 5' to 3' direction a promoter sequence and the DNA sequence using
(i) a forward primer comprising
at its 3' end, a first sequence part complementary to a promoter region of the source expression polynucleotide upstream of the DNA sequence, and
at its 5' end a second sequence part comprising one or more introduced control element(s); and
(ii) a reverse primer selected from
a reverse primer complementary to a region of the source expression polynucleotide downstream of the DNA sequence, and wherein the primer comprises mRNA destabilization or stabilization elements of a 3' UTR of a cellular mRNA and a termination sequence, or
a reverse primer complementary to a region of the source expression polynucleotide downstream of 3' UTR wherein the region contains mRNA destabilization or stabilization elements of a 3' UTR of a cellular mRNA,
wherein the source expression polynucleotide is a vector, a lentivirus, a plasmid, a virus-based vector, or a linear or linearized or amplified fragment thereof,
wherein the mRNA destabilization elements are selected from AU-rich elements, GU-rich elements, and U-rich sequences,
wherein the mRNA stabilization elements are selected from GC-rich elements, CU-rich elements, and UG-rich sequences,
wherein the generating step does not involve a cloning step, wherein said cloning step includes the use of any one or more of restriction digestion, cloning enzyme(s), bacterial transformation and plasmid preparation, and
wherein expression of the inducible expression active linear gene construct resulting from (a) can be induced by the addition of a compound that activates the expression or by the withdrawal of a compound that represses the expression.

15. The method of claim 14, further comprising the following steps:
(b) transfecting a cell or cell line with the repressible expression active linear gene construct obtained in step (a) of claim 14; wherein the cell or cell line transiently or stably expresses a repressor system,
(c) expressing a protein encoded by the DNA sequence contained in the repressible expression active linear gene construct obtained in step (a) of claim 14 by the addition of a compound that represses the expression or by the withdrawal of a compound that activates the expression; and
(d) measuring gene expression level or activity of the protein expressed in step (c).

16. The method according to claim 14, wherein the minimal promoter is RPS23 promoter or RPS30 promoter, which is modified for higher expression by modifying the transcriptional initiation sequence.

17. The method according to claim 14, wherein the termination sequence comprises an eukaroytic polyadenylation signal, pol III termination signal, thymidines stretch, U1 termination signal, pol I termination signal, or a synthetic termination variant.

18. The method according to claim 14, wherein the repressible expression element is selected from the group consisting of a tetracycline (TetO) system, a heat shock off system, a lacO/IPTG system, a cre system, a nitroreductase system, a coumermycin/novobiocin-regulated system, a RheoSwitch Ligand RSL1 system, a chimeric bipartite nuclear receptor expression system, a GAL4 system.

19. The method according to claim 14, wherein the forward primer comprises one or more regulatory sequence element(s) or transcriptional element(s) selected from transcriptional enhancing and translational enhancing element(s).

20. The method according to claim 14, wherein the forward primer comprises a nucleic acid sequence selected from of SEQ ID NOs. 13 or 14.

21. The method according to claim 14, wherein the DNA sequence encodes a gene which is selected from the group consisting of: reporters, fluorescent reporters, green fluorescent protein (GFP) and derivatives, enhanced green fluorescent protein (EGFP) and derivatives, luciferase, modified luciferase, inhibitory RNA coding sequences, secreted reporter forms, alkaline phosphatase, CAT, β-galactosidase, antibodies, immunoglobin fragments, cDNA fragments, open reading frames (ORF), and domain sequences.

* * * * *

UNITED STATES PATENT AND TRADEMARK OFFICE
CERTIFICATE OF CORRECTION

PATENT NO.       : 8,680,256 B2
APPLICATION NO.  : 13/001303
DATED            : March 25, 2014
INVENTOR(S)      : Khalid S. Abu Khabar It is certified that error appears in the above-identified patent and that said Letters Patent is hereby corrected as shown below:

In the Specification

Column 6,
Line 61, "First" should read --(first--

Column 18,
Line 47, "TTACGTCA" should read --TTACGTCA--

Column 18,
Lines 47-48, "TTATGTCA-" should read --TTATGTCA--

Column 22,
Line 23, "thereof" should read --thereof.--

Column 59,
Line 43, "the inducible expression" should read --the repressible expression--

Column 59,
Line 44, "can be induced by" should read --can be repressed by--

Column 59,
Line 45, "that activates the expression" should read --that represses the expression--

Column 59,
Line 46, "that represses the expression." should read --that activates the expression.--

Signed and Sealed this
Twelfth Day of August, 2014

Michelle K. Lee
*Deputy Director of the United States Patent and Trademark Office*

SEQUENCE LISTING

<160> NUMBER OF SEQ ID NOS: 32

<210> SEQ ID NO 1
<211> LENGTH: 3504
<212> TYPE: DNA
<213> ORGANISM: Homo sapiens

<400> SEQUENCE: 1
agcgtggcct tgtttgtacc tccatgattg cctggctggc cttgctaacc taatcacatc    60
tgtgacggga tatagtgatg tttaatctta tgattgcctt aagaattaag gcaatcagac   120
gggttcggcg gctcatgcct gtaatcccag cactttggga ggccgaggcg ggcggatcac   180
gaggtcagaa gatccagtcc atcctggcta caaggtgaa accccgtctc tactaaaaat    240
acaaaaaatt agccgggcat ggtggcggga gcctgtagtc ccagctactc gggaggctga   300
ggcaggagga tggcgtgaat ctggaggcg gagcttgcag tgggccgaga tcgcgccact   360
gccctccagc ctgggcgaca gagcgagact ccgtctcaaa aaaaaaaaaa aaagaatta   420 aggcaatcat aattccccac gcacactcat atgctaggac cccgccccctt acctgaaacg   480

```
ttgtggctta tatagacact gccaggcact gtgttaagtg ctcccaaaga gcacccagt      540 ctaccatttt ccctctcgat tctatatgta cactcgggac aagttctcct gatcgaaaac    600
ggcaaaacta aggccccaag taggaatgcc ttagttttcg ggttaacaa tgattaacac     660 tgagcctcac acccacgcga tgccctcagc tcctcgctca gcgctctcac caacagccgt    720
agcccgcagc cccgctggac accggttctc catccccgca gcgtagcccg gaacatggta    780
gctgccatct ttacctgcta cgccagcctt ctgtgcgcgc aactgtctgg tcccgccccg    840
tcctgcgcga gctgcctgcc caggcaggtt cgccggtgcg agcgtaaagg ggcggagcta    900
ggactgcctt gggcggtaca aatagcaggg aaccgcgcgg tcgctcagca gtgacgtgac    960
acgcagccca cggtctgtac tgacgcgccc tcgcttcttc ctctttctcg actccatctt   1020
cgcggtagct gggaccgccg ttcaggtaag aatgggcct tggctggatc cgaagggctt    1080
gtagcaggtt ggctgcgggg tcagaaggcg cgggggaac cgaagaacgg ggcctgctcc    1140
gtggccctgc tccagtccct atccgaactc cttgggaggc ctggccttcc ccacgtgagc   1200
cgccgcgacc accatcccgt cgcgatcgtt tctggaccgc tttccactcc caaatctcct   1260
ttatcccaga gcatttcttg gcttctctta caagccgtct tttctttact cagtcgccaa   1320
tatgcagctc tttgtccgcg cccaggagct acacaccttc gaggtgaccg gccaggaaac   1380
ggtcgcccag atcaaggtaa ggctgcttgg tgcgccctgg gttccatttt cttgtgctct   1440
tcactctcgc ggcccgaggg aacgcttacg agccttatct ttccctgtag gctcatgtag   1500
cctcactgga gggcattgcc ccggaagatc aagtcgtgct cctggcaggc gcgcccctgg   1560
aggatgaggc cactctgggc cagtgcgggg tggaggccct gactaccctg gaagtagcag   1620
gccgcatgct tggaggtgag tgagagagga atgttctttg aagtaccggt aagcgtctag   1680
tgagtgtggg gtgcatagtc ctgacagctg agtgtcacac ctatggtaat agagtacttc   1740
tcactgtctt cagttcagag tgattcttcc tgtttacatc cctcatgttg aacacagacg   1800
tccatgggag actgagccag agtgtagttg tatttcagtc acatcacgag atcctagtct   1860
ggttatcagc ttccacacta aaattaggtc agaccagggc ccccaaagtg ctctataaaa   1920
ttagaagctg aagatcctg aaatgaaact taagatttca aggtcaaata tctgcaactt    1980
tgttctcatt acctattggg cgcagcttct ctttaaaggc ttgaattgag aaaagagggg   2040
ttctgctggg tggcaccttc ttgctcttac ctgctggtgc cttcctttcc cactacaggt   2100
aaagtccatg gttccctggc ccgtgctgga aaagtgagag gtcagactcc taaggtgagt   2160
gagagtatta gtggtcatgg tgttaggact ttttttcctt tcacagctaa accaagtccc   2220
tgggctctta ctcggtttgc cttctccctc cctggagatg agcctgaggg aagggatgct   2280
aggtgtggaa gacaggaacc agggcctgat taaccttccc ttctccaggt ggccaaacag   2340
gagaagaaga agaagaagac aggtcgggct aagcggcgga tgcagtacaa ccggcgcttt   2400
gtcaacgttg tgcccacctt tggcaagaag aagggcccca atgccaactc ttaagtcttt   2460
tgtaattctg gctttctcta ataaaaagc cacttagttc agtcatcgca ttgtttcatc    2520
tttacttgca aggcctcagg gagaggtgtg cttctcgggt tggtggtatg tcccctagga   2580
gaacagtgag gcagaaaagg cagaagcctt tggtatgggg ggaagaaatg gtaaactaca   2640
agagaaattt cctgtgaaga aacagctaca gatcctgggg ggcttcagat gtaaaattgg   2700
ggttattccc tatcctaagt aacttgatca gtcccccag gtcattcttt ttcatcttct    2760
aaacagagaa ggtagcagga atcactgtgg tgagaggttt gttatggagg cagcaataga   2820
agggatgggt gggggaagag gtttgtatag aaggtgaacc tggccgttcc ctgaacttgg   2880
```

```
taccagctgt ggccttagag tccagggcag gaatctggtc tgccttggtt ttagaagtaa   2940
atattatgtt gggagcatgg cctgttttgt acctctgtga ctgcctggcc ggacttggta   3000
acctaatcac atctgtgatt ggatatagtg aggtttcagt gttcccaaaa gttgggttac   3060
ctctggggct gattcagggt tctcttctgg caactgagcc tcccagcact ctgaaccccc   3120
acttactcat tcagctaaag tttctggacc tgccagttct tgagaaatag catccaacag   3180
ggtaaagccc ttgggctgtg actttgact gcctgagttt ggaccttctt tttcttccta    3240
ctccatttac tgggtggctg cctttgaac taactactaa tttaatctct gccatctcca    3300
gggctgctgt gagggttaaa ggatgtaaat caacatctgg cttacagtga gtgtgtgaat   3360
cttggctatt tttgtctctg tggtgttaaa acatggtttt ctgccttcca gcagtttaga   3420
aaggggagg atgtgacag atacaatagc atcccagaga gggcctcttt ttttgttttt     3480
cttttttctt tattttattt tatt                                          3504
```

<210> SEQ ID NO 2
<211> LENGTH: 4289
<212> TYPE: DNA
<213> ORGANISM: Homo sapiens

<400> SEQUENCE: 2

```
gtctggcaca tagaaggcat ttttaaacat ccttgctgag tgaaccaata tcccagaaac    60
ctctcacagc tagttcatct tacaggagaa acagtattaa agagttaatt aaatggccag   120
gcgcggtggc tcacgcctgt aatcccagca cattgggagg ccgaggcggg cggatcactc   180
gaggtcagga gatcgacacc agcctggcca acatggtgaa accccctctc tactgaaaat   240
acaaacatca gccaggcgtg atggtggaag cctgtaatcc cagctactca ggaggctgag   300
gtgggacaat cgcttgaacc cgggaggcgg aggttgtagt gagccaagat cgcaccactg   360
cacaacagcc tagaagacag agtgagaccc tgtctcagaa aaaataaaa ataaaaataa     420
ataaatctat aagtaaatga ctcgccagtc aaaataaacg gcaactttag ggttaaaggc   480
ccaatctggc tccaaagctt ggggttttag ttactacact acattgcttc actatatttt   540
acaatttact agctgcttat aagtatgaat taaggctcag aagtctaatt ttccagacta   600
ctcggaggac tctcgcccca ctccactcca caaagattca gctcagcgac tccttcctac   660
tctgacctag ccccgcgtcc cgctctcagt ggcttgggca agagcgcctg cgcggtgagc   720
gggtcccata aaacgcattc tgggattggt agtccatgtt cctccggtct ccagcattca   780
aaagaaaaag ggggaaaaaa aaccatgcaa attagatatc tctgaatttc ttgcaaatta   840
aataagacgc agattctggc tcaggaaagt gatgcaaacg cgtcgttttc aaaggagaga   900
ccccagcctc gggtcaggcg cggcgcagac agcggcgcgg ggtccttggc tgggcggggc   960
ttgctcgcgg tggcttgtgg ctccttcctg cggtgcttct ctctttcgct caggcccgtg  1020
gcgccgacag gatgggtgag ctgttgtggc cggtttaagg gcgctgcaag cgggacttgg  1080
ggtcttgggg acgggcgggc ggatgcgaat agagtagggc gggggatgcc atggagaggc  1140
tccatggggg agggccgggg aagcgccgct ccaggaggca cgtggtccgg cgcggaaggg  1200
gcccatgagg cgtggaggcc gccgaggtcg gggtaccgag ggacgcaggg aggccagcgc  1260
ttcctcccgg gcattcgagc ggggcctcgt ccttcgggag aacacattct ccggagccct  1320
cttcgaacgt ttattagtcg gttcagggca acttgaaggc caaatgtttg gcccacaggc  1380
caataaatag tacgagagcc aatcggctta agggtttatt ccaggtgagg cgagtgtctt  1440
agaagatggg aaacacgtag atggcgtgtt tttacggaag aactaaaata tttaattttt  1500
```

```
aggcaagtgt cgtggacttc gtactgctag gaagctccgt agtcaccgac gagaccagaa    1560
gtggcatgat aaacagtata agaaagctca tttgggcaca gccctaaagg ccaacccttt    1620
tggaggtgct tctcatgcaa aaggaatcgt gctggaaaaa gtgtaagtcc attgctcccg    1680
tcaagtttta gttattata ggaattcgag acatgaactt acgaattctt gttttgaaag    1740
taattgcagg ttttgtgta gtagtattca tttgggcatt gtgggtaaa attgcaaagc    1800 gtttgttcta tttaaaagtt ggtaaaatta gtttttggga attaggtagt taaggtttta    1860
atttaacgtt ggcctggaag gaattggaga agatactagc aatgatgaag taaaggacac    1920
aaacaccttt actgtgggag ttgttataag taaatggcac gtgtcagcta ttgaacttta    1980
tcgacttgat aaaactaagg tgaagagaag tgacttgcat cagaattaat tgaggtcata    2040
cacctaagat tgagacatga aactgccagt atttgactgg ttttgacttt ttaaaataat    2100
aatttcatat agttctatca tatttgatgg tagagccatt ttaacccaga cttttttttt    2160
tttttttttt tttttgaga cagtctagct ctgtcaccca ggctggtgtg cagtagcgca    2220
agactccctg caaccttagc ctcccaggtt caagcatttc tcctgcctca gcctcccagg    2280
tagctgggat tacaggcgcc cactaccaca ccagctaata ttttgtattt tcagtagtga    2340
tggggtttca ccatgttgac caggctagtc tcaaactcct gacctcaggt gataatgcct    2400
gcttcggcct ccgaaagtgc tggaattaca ggcgtgagcc actgtgtccg cccagactt    2460 tctaattctt acctcagata cctttttttct tttttctttt ttttttttg agatagggtc    2520 ccttgtcaca caggctggcc atcttgacgt tctaggcata gatcctccca cgtcagcctc    2580
gcaagtagtt gggactacag gcccacgctg ccactccagt ctacttttat aactgtaaaa    2640
ggtctagaaa tttcccccat tgtgctaatg aaattaagac tggcagaaaa ctaggttgac    2700
atcacaggac ttcagctcag ccatttgagg ttagattgaa aagatagaaa cagtttctca    2760
ttagttctct agttaatatg aaaagataat cttttcaga aagccagctc acagtgctgt    2820
gccttttgta tttcagagga gttgaagcca aacagccaaa ttctgccatt aggaagtgtg    2880
taagggtcca gctgatcaag aatggcaaga aaatcacagc ctttgtaccc aatgacggtt    2940
gcttgaactt tattgaggtg agtatttcaa ctctatcgta ccttctgttc ttggggtggc    3000
ctccctcaca ttttatctg atgcaaggga gtttcctcac atgaaagtat ttttgtgatc    3060
gccaccaaca ccagaaataa acttcttatt ttattccagg aaaatgatga agttctggtt    3120
gctggatttg gtcgcaaagg tcatgctgtt ggtgatattc ctggagtccg ctttaaggtt    3180
gtcaaagtag ccaatgtttc tcttttggcc ctatacaaag gcaagaagga aagaccaaga    3240
tcataaatat taatggtgaa aacactgtag taataaattt tcatatgcca aaaaatgttt    3300
gtatcttact gtccctgtt ctcaccacga agatcatgtt cattaccacc accacccccc    3360
cttatttttt ttatcctaaa ccagcaaacg caggacctgt accaattta ggagacaata    3420 agacagggtt gtttcaggat tctctagagt taataacatt tgtaacctgg cacagtttcc    3480
ctcatcctgt ggaataagaa aatgggatag atctggaata aatgtgcagt attgtagtat    3540
tactttaaga actttaaggg aacttcaaaa actcactgaa attctagtga gatactttct    3600
tttttattct tggtatttc catatcgggt gcaacacttc agttaccaaa tttcattgca    3660
catagattat cttaggtacc cttggaaatg cacattcttg tatccatctt acaggggccc    3720
aagatgataa atagtaaact caaaattgct ccccactctg tttattattt aaaggtgtca    3780
ggatctgtgt tgtaatgtgt ctacattaat gtgtttagga gaatacaggc attggatcat    3840
ttagttgatg gaagtatatg ccaggcaagg gagataaggt atacgacaag actgatgttt    3900
```

```
tcagtatctt ctcatgaggt tgtcagagac cttcatgtct tcaaagacta gtcagcaaat    3960
gaagtggttt agtgtagaga caagattggt tgtgttttga taatttaagc taggtattga    4020
gtacatgtgg attttgctgt ccacaaatac ttgtttcaga gttttcatgg atacagtggc    4080
atggttgaaa tgaagctgtg agccttctgc tttaaatctg atgtaagaaa ctcctgttaa    4140
caaatagtaa gtatgggtta attagccctt tgatcaaagc ctagctttac attgtttagg    4200
atctttggaa aacaattggt ttggttgccc actttccgta ggatcaagag cagaaccttt    4260
cacatggcac agaagaaccc aggttgcgc                                      4289

<210> SEQ ID NO 3
<211> LENGTH: 733
<212> TYPE: DNA
<213> ORGANISM: Artificial
<220> FEATURE:
<223> OTHER INFORMATION: modified RPS30 promoter region

<400> SEQUENCE: 3
gatatcggca aaactaaggc cccaagtagg aatgccttag ttttcggggt taacaatgat     60
taacactcct gagcctcaca cccacgcgat gccctcagct cctcgctcag cgctctcacc    120
aacagccgta gcccgcagcc ccgctggaca ccgggtctcc atccccgcag cgtagcccgg    180
aacatggtag ctgccatctt tacctgctac gccagccttc tgtgcgcgca actgtctggt    240
cccgccccgt cctgcgcgag ctgcctgccc aggcaggttc gccggtgcga gcgtaaaggg    300
gcggagctag gactgccttg gcggtatataa atagcaggga accgcgcggt cgctcagcag    360
tgacgtgaca cgcagcccac ggtctgtact gacgcgccct cgcttcttcc tctttctcga    420
ctccatcttc gcggtagctg ggaccgccgt tcaggtaaga atggggcctt ggctgcagcc    480
gaagggcttg tagcaggttg gctgcggggt cagaaggcgc ggggggaacc gaagaacggg    540
gcctgctccg tggccctgct ccagtcccta tccgaactcc ttgggaggcc tggccttccc    600
cacgtgagcc gccgcgacca ccatcccgtc gcgatcgttt ctggaccgct ttccactccc    660
aaatctcctt tatcccagag catttcttgg cttctcttac aagccgtctt ttctttactc    720
agtcgccgtc gac                                                       733

<210> SEQ ID NO 4
<211> LENGTH: 781
<212> TYPE: DNA
<213> ORGANISM: Artificial
<220> FEATURE:
<223> OTHER INFORMATION: modified RPS30 promoter region

<400> SEQUENCE: 4
gatatctagc cgggcatggt ggcgggagcc tgtagtccca gctactcggg aggctgaggc     60
aggaggatgg cgtgaatctg ggaggcggag cttgcagtgg gccgagatcg cgccacttga    120
gcctcacacc cacgcgatgc cctcagctcc tcgctcagcg ctctcaccaa cagccgtagc    180
ccgcagcccc gctggacacc gggtctccat ccccgcagcg tagcccggaa catggtagct    240
gccatcttta cctgctacgc cagccttctg tgcgcgcaac tgtctggtcc cgccccgtcc    300
tgcgcgagct gcctgcccag gcaggttcgc cggtgcgagc gtaaaggggc ggagctagga    360
ctgccttggg cggtacaaat agcagggaac cgcgcggtcg ctcagcagtg acgtgacacg    420
cagcccacgg tctgtactga cgcgccctcg cttcttcctc tttctcgact ccatcttcgc    480
ggtagctggg accgccgttc aggtaagaat ggggccttgg ctgcagccga agggcttgta    540
gcaggttggc tgcggggtca gaaggcgcgg ggggaaccga agaacggggc tgctccgtg    600
```

```
gccctgctcc agtccctatc cgaactcctt gggaggcctg gccttcccca cgtgagccgc    660
cgcgaccacc atcccgtcgc gatcgtttct ggaccgcttt ccactcccaa atctccttta    720
tcccagagca tttcttggct tctcttacaa gccgtctttt ctttactcag tcgccgtcga    780
c                                                                    781

<210> SEQ ID NO 5
<211> LENGTH: 781
<212> TYPE: DNA
<213> ORGANISM: Artificial
<220> FEATURE:
<223> OTHER INFORMATION: modified RPS30 promoter region

<400> SEQUENCE: 5
gatatctagc cgggcatggt ggcgggagcc tgtagtccca gctactcggg aggctgaggc     60
aggaggatgg cgtgaatctg ggaggcggag cttgcagtgg gccgagatcg cgccacttga    120
gcctcacacc cacgcgatgc cctcagctcc tcgctcagcg ctctcaccaa cagccgtagc    180
ccgcagcccc gctggacacc gggtctccat ccccgcagcg tagcccggaa catggtagct    240 gccatctttta cctgctacgc cagccttctg tgcgcgcaac tgtctggtcc cgccccgtcc    300
tgcgcgagct gcctgcccag gcaggttcgc cggtgcgagc gtaaagggggc ggagctagga    360 ctgccttggg cggtataaat agcagggaac cgcgcggtcg ctcagcagtg acgtgacacg    420
cagcccacgg tctgtactga cgcgccctcg cttcttcctc tttctcgact ccatcttcgc    480
ggtagctggg accgccgttc aggtaagaat ggggccttgg ctgcagccga agggcttgta    540
gcaggttggc tgcggggtca gaaggcgcgg ggggaaccga agaacggggc ctgctccgtg    600
gccctgctcc agtccctatc cgaactcctt gggaggcctg gccttcccca cgtgagccgc    660
cgcgaccacc atcccgtcgc gatcgtttct ggaccgcttt ccactcccaa atctccttta    720
tcccagagca tttcttggct tctcttacaa gccgtctttt ctttactcag tcgccgtcga    780
c                                                                    781

<210> SEQ ID NO 6
<211> LENGTH: 992
<212> TYPE: DNA
<213> ORGANISM: Artificial
<220> FEATURE:
<223> OTHER INFORMATION: modified RPS23 promoter region

<400> SEQUENCE: 6
gatatctggc caggcgcggt ggctcacgcc tgtaatccca gcacattggg aggccgaggc     60
gggcggatca ctcccagact actcggagga ctctcgcccc actccactcc acaaagattc    120
agctcagcga ctccttccta ctctgaccta gccccgcgtc ccgctctcag tggcttgggc    180
aagagcgcct gcgcggtgag cgggtcccat aaaacgcatt ctgggattgg tagtccatgt    240
tcctccggtc tccagcattc aaaagaaaaa gggggaaaaa aaaccatgca aattagaatc    300
tctgaatttc ttgcaaatta aataagacgc agattctggc tcaggaaagt gatgcaaacg    360
cgtcgttttc aaaggagaga ccccagcctc gggtcaggcg cggcgcagac agcggcgcgg    420
ggtccttggc tgggcggggc ttgctcgcgg tggcttgtgg ctccttcctg cggtgcttct    480
ctctttcgct caggcccgtg gcgccgacag gctgggtgag ctgttgtggc cggtttaagg    540
gcgctgcaag cgggacttgg ggtcttgggg acgggcgggc ggatgcgaat agagtagggc    600
gggggatgcc atgagaggc tcatggggg agggccgggg aagcgccgct ccaggaggca    660
cgtggtccgg cgcggaaggg gcccatgagg cgtggaggcc gccgaggtcg gggtaccgag    720
```

-continued

```
ggacgcaggg aggccagcgc ttcctcccgg gcattcgagc ggggcctcgt ccttcgggag    780
aacacattct ccggagccct cttcgaacgt ttattagtcg gttcagggca acttgaaggc    840
caaatgtttg cccacaggc caataaatag tacgagagcc aatcggctaa gggtttattc     900
caggtgaggc gagtgtctta gaagatggga aacacgtaga tggcgtgttt ttacggaaga    960
actaaaatat ttaattttta ggcaaggtcg ac                                  992
```

<210> SEQ ID NO 7
<211> LENGTH: 793
<212> TYPE: DNA
<213> ORGANISM: Artificial
<220> FEATURE:
<223> OTHER INFORMATION: modified RPS30 promoter region

<400> SEQUENCE: 7

```
gatatcggca aaactaaggc cccaagtagg aatgccttag ttttcggggt taacaatgat    60
taacactcct gagcctcaca cccacgcgat gccctcagct cctcgctcag cgctctcacc    120
aacagccgta gcccgcagcc ccgctggaca ccgggtctcc atccccgcag cgtagcccgg    180
aacatggtag ctgccatctt tacctgctac gccagcctttc tgtgcgcgca actgtctggt    240
cccgccccgt cctgcgcgag ctgcctgccc aggcaggttc gccggtgcga gcgtaaaggg    300
gcggagctag gactgccttg ggcggtataa atagcaggga catccctatc agtgatagac    360
catccctatc agtgatagac catccctatc agtgatagac accgcgcggt cgctcagcag    420
tgacgtgaca cgcagcccac ggtctgtact gacgcgccct cgcttcttcc tctttctcga    480
ctccatcttc gcggtagctg ggaccgccgt tcaggtaaga atggggcctt ggctgcagcc    540
gaagggcttg tagcaggttg gctgcggggt cagaaggcgc ggggggaacc gaagaacggg    600
gcctgctccg tggccctgct ccagtcccta tccgaactcc ttgggaggcc tggccttccc    660
cacgtgagcc gccgcgacca ccatcccgtc gcgatcgttt ctggaccgct ttccactccc    720
aaatctcctt tatcccagag catttcttgg cttctcttac aagccgtctt ttctttactc    780
agtcgccgtc gac                                                       793
```

<210> SEQ ID NO 8
<211> LENGTH: 793
<212> TYPE: DNA
<213> ORGANISM: Artificial
<220> FEATURE:
<223> OTHER INFORMATION: modified RPS30 promoter region

<400> SEQUENCE: 8

```
gatatcggca aaactaaggc cccaagtagg aatgccttag ttttcggggt taacaatgat    60
taacactcct gagcctcaca cccacgcgat gccctcagct cctcgctcag cgctctcacc    120
aacagccgta gcccgcagcc ccgctggaca ccgggtctcc atccccgcag cgtagcccgg    180
aacatggtag ctgccatctt tacctgctac gccagcctttc tgtgcgcgca actgtctggt    240
cccgccccgt cctgcgcgag ctgcctgccc aggcaggttc gccggtgcga gcgtaaaggg    300
gcatccctat cagtgataga ccatccctat cagtgataga ccatccctat cagtgataga    360
ccggagctag gactgccttg ggcggtataa atagcaggga accgcgcggt cgctcagcag    420
tgacgtgaca cgcagcccac ggtctgtact gacgcgccct cgcttcttcc tctttctcga    480
ctccatcttc gcggtagctg ggaccgccgt tcaggtaaga atggggcctt ggctgcagcc    540
gaagggcttg tagcaggttg gctgcggggt cagaaggcgc ggggggaacc gaagaacggg    600
gcctgctccg tggccctgct ccagtcccta tccgaactcc ttgggaggcc tggccttccc    660
```

```
cacgtgagcc gccgcgacca ccatcccgtc gcgatcgttt ctggaccgct ttccactccc      720
aaatctcctt tatcccagag catttcttgg cttctcttac aagccgtctt ttctttactc      780
agtcgccgtc gac                                                         793
```

```
<210> SEQ ID NO 9
<211> LENGTH: 18
<212> TYPE: DNA
<213> ORGANISM: Artificial
<220> FEATURE:
<223> OTHER INFORMATION: TetO sequence

<400> SEQUENCE: 9
atccctatca gtgataga                                                     18

<210> SEQ ID NO 10
<211> LENGTH: 19
<212> TYPE: DNA
<213> ORGANISM: Artificial
<220> FEATURE:
<223> OTHER INFORMATION: TetO sequence

<400> SEQUENCE: 10
tccctatcag tgatagaga                                                    19

<210> SEQ ID NO 11
<211> LENGTH: 16
<212> TYPE: DNA
<213> ORGANISM: Artificial
<220> FEATURE:
<223> OTHER INFORMATION: TetO sequence

<400> SEQUENCE: 11
ctatcagtga tagaga                                                       16

<210> SEQ ID NO 12
<211> LENGTH: 13
<212> TYPE: DNA
<213> ORGANISM: Artificial
<220> FEATURE:
<223> OTHER INFORMATION: TetO sequence

<400> SEQUENCE: 12
tcagtgatag aga                                                          13

<210> SEQ ID NO 13
<211> LENGTH: 6
<212> TYPE: DNA
<213> ORGANISM: Artificial
<220> FEATURE:
<223> OTHER INFORMATION: minimal TetO sequence

<400> SEQUENCE: 13 tgatag                                                                   6

<210> SEQ ID NO 14
<211> LENGTH: 19
<212> TYPE: DNA
<213> ORGANISM: Artificial
<220> FEATURE:
<223> OTHER INFORMATION: TetO sequence

<400> SEQUENCE: 14
actctatcat tgatagagt                                                    19

<210> SEQ ID NO 15
```

```
<211> LENGTH: 75
<212> TYPE: DNA
<213> ORGANISM: Artificial
<220> FEATURE:
<223> OTHER INFORMATION: Forward primer

<400> SEQUENCE: 15
catccctatc agtgatagac catccctatc agtgatagac catccctatc agtgatgagg      60
cgtatgaggc tgtgt                                                       75

<210> SEQ ID NO 16
<211> LENGTH: 74
<212> TYPE: DNA
<213> ORGANISM: Artificial
<220> FEATURE:
<223> OTHER INFORMATION: Forward primer

<400> SEQUENCE: 16
catccctatc agtgatagac catccctatc agtgatagac catccctatc agtgatagtg      60
cgcggggcaa gtga                                                        74

<210> SEQ ID NO 17
<211> LENGTH: 77
<212> TYPE: DNA
<213> ORGANISM: Artificial
<220> FEATURE:
<223> OTHER INFORMATION: Forward primer

<400> SEQUENCE: 17
catccctatc agtgatagac catccctatc agtgatagac catccctatc agtgatgtga      60
ccgtgtgtgt aaagagt                                                     77

<210> SEQ ID NO 18
<211> LENGTH: 21
<212> TYPE: DNA
<213> ORGANISM: Artificial
<220> FEATURE:
<223> OTHER INFORMATION: Reverse primer

<400> SEQUENCE: 18
ccagtctact tttgaaactc c                                                21

<210> SEQ ID NO 19
<211> LENGTH: 77
<212> TYPE: DNA
<213> ORGANISM: Artificial
<220> FEATURE:
<223> OTHER INFORMATION: Forward primer

<400> SEQUENCE: 19
catccctatc agtgatagac catccctatc agtgatagac catccctatc agtgatggac      60
tatcatatgc ttaccgt                                                     77

<210> SEQ ID NO 20
<211> LENGTH: 17
<212> TYPE: DNA
<213> ORGANISM: Artificial
<220> FEATURE:
<223> OTHER INFORMATION: Reverse primer

<400> SEQUENCE: 20
acgacggcca gtgccaa                                                     17

<210> SEQ ID NO 21
```

```
<211> LENGTH: 54
<212> TYPE: DNA
<213> ORGANISM: Artificial
<220> FEATURE:
<223> OTHER INFORMATION: Primer

<400> SEQUENCE: 21
catccctatc agtgatagac catccctatc agtgatagac catccctatc agtg        54

<210> SEQ ID NO 22
<211> LENGTH: 64
<212> TYPE: DNA
<213> ORGANISM: Artificial
<220> FEATURE:
<223> OTHER INFORMATION: Primer

<400> SEQUENCE: 22
accaggtccc tatcagtgat agagatcctc cctatcagtg atagagaggt aggcgtgtac    60
ggtg                                                                64

<210> SEQ ID NO 23
<211> LENGTH: 76
<212> TYPE: DNA
<213> ORGANISM: Artificial
<220> FEATURE:
<223> OTHER INFORMATION: Primer

<400> SEQUENCE: 23
gaaaaaagaa gaggcaatta ccagttttga caggaagaaa ctggtaattg cctcttctcg    60
gttcactaaa cgagct                                                   76

<210> SEQ ID NO 24
<211> LENGTH: 76
<212> TYPE: DNA
<213> ORGANISM: Artificial
<220> FEATURE:
<223> OTHER INFORMATION: Primer

<400> SEQUENCE: 24
gaaaaaagaa gaggcaatta ccagttttga caggaagaaa ctggtaattg cctcttctcg    60
agatcttggg cctctg                                                   76

<210> SEQ ID NO 25
<211> LENGTH: 72
<212> TYPE: DNA
<213> ORGANISM: Artificial
<220> FEATURE:
<223> OTHER INFORMATION: Primer

<400> SEQUENCE: 25
aaaagaagag gcaattacca gttttgacag gaagaaactg gtaattgcct cttctcgcgt    60
cctttccaca ag                                                       72

<210> SEQ ID NO 26
<211> LENGTH: 67
<212> TYPE: DNA
<213> ORGANISM: Artificial
<220> FEATURE:
<223> OTHER INFORMATION: Primer

<400> SEQUENCE: 26
aagaagaggc aattaccagt ttctcttgaa aactggtaat tgcctcttcc ggttcactaa    60
acgagct                                                             67
```

```
<210> SEQ ID NO 27
<211> LENGTH: 81
<212> TYPE: DNA
<213> ORGANISM: Artificial
<220> FEATURE:
<223> OTHER INFORMATION: Forward primer

<400> SEQUENCE: 27
catccctatc agtgatagac catccctatc agtgatagac catccctatc agtgatagac      60
gctgcctgcc caggcaggtt c                                                81

<210> SEQ ID NO 28
<211> LENGTH: 80
<212> TYPE: DNA
<213> ORGANISM: Artificial
<220> FEATURE:
<223> OTHER INFORMATION: Forward primer

<400> SEQUENCE: 28
catccctatc agtgatagac catccctatc agtgatagac catccctatc agtgatagac      60
ggcggagcta ggactgcctt                                                  80

<210> SEQ ID NO 29
<211> LENGTH: 82
<212> TYPE: DNA
<213> ORGANISM: Artificial
<220> FEATURE:
<223> OTHER INFORMATION: Forward primer

<400> SEQUENCE: 29
accaggtccc tatcagtgat agagatcctc cctatcagtg atagagactg ggtatataat      60
ggaagccacc atggccagca ag                                               82

<210> SEQ ID NO 30
<211> LENGTH: 64
<212> TYPE: DNA
<213> ORGANISM: Artificial
<220> FEATURE:
<223> OTHER INFORMATION: Reverse primer

<400> SEQUENCE: 30
accaggtccc tatcagtgat agagatcctc cctatcagtg atagagactg ggtatataat      60
ggaa                                                                   64

<210> SEQ ID NO 31
<211> LENGTH: 8
<212> TYPE: DNA
<213> ORGANISM: Artificial
<220> FEATURE:
<223> OTHER INFORMATION: cAMP response element

<400> SEQUENCE: 31 ttacgtca                                                                8

<210> SEQ ID NO 32
<211> LENGTH: 8
<212> TYPE: DNA
<213> ORGANISM: Artificial
<220> FEATURE:
<223> OTHER INFORMATION: cAMP response element

<400> SEQUENCE: 32 ttatgtca                                                                8
```